United States Patent
Rogelj et al.

(10) Patent No.: US 10,414,778 B2
(45) Date of Patent: Sep. 17, 2019

(54) METHODS FOR TREATMENT OF RESISTANT CANCER

(71) Applicant: New Mexico Tech University Research Park Corporation, Socorro, NM (US)

(72) Inventors: Snezna Rogelj, Socorro, NM (US); Liliya Frolova, Socorro, NM (US); Alexander Kornienko, San Marcos, TX (US); Sean Henry, Ann Arbor, MI (US)

(73) Assignee: NEW MEXICO TECH UNIVERSITY RESEARCH PARK CORPORATION, Socorro, NM (US)

( * ) Notice: Subject to any disclaimer, the term of this patent is extended or adjusted under 35 U.S.C. 154(b) by 0 days.

(21) Appl. No.: 15/498,788

(22) Filed: Apr. 27, 2017

(65) Prior Publication Data

US 2017/0313720 A1    Nov. 2, 2017

Related U.S. Application Data

(60) Provisional application No. 62/364,891, filed on Jul. 21, 2016, provisional application No. 62/341,120, filed on May 25, 2016, provisional application No. 62/329,393, filed on Apr. 29, 2016.

(51) Int. Cl.
*A61K 31/4748* (2006.01)
*C07D 495/18* (2006.01)
*C07D 491/18* (2006.01)
*C07D 471/08* (2006.01)

(52) U.S. Cl.
CPC ......... *C07D 495/18* (2013.01); *C07D 471/08* (2013.01); *C07D 491/18* (2013.01)

(58) Field of Classification Search
CPC ............................ C07D 471/08; C07D 471/02
USPC ..................................... 546/72, 71; 514/289
See application file for complete search history.

(56) References Cited

U.S. PATENT DOCUMENTS 6,638,925 B2 * 10/2003 Czollner .............. C07D 471/08
                                                           514/212.02
2006/0111341 A1 *  5/2006 Bodenteich et al. .. A61K 31/55
                                                           514/215

FOREIGN PATENT DOCUMENTS

WO    WO-2017189834 A1    11/2017

OTHER PUBLICATIONS

Feinstein, A.I. et al.: Biosynthetic oxidation and rearrangement of Vittatine and its derivatives. J. Org. Chem., vol. 41, pp. 2447-2450, 1976.*
Fales, H.M. et al.: Alkaloids of the Amaryllidaceae. XIX. On the structures of Crinamidine, Flexinine, and Nerbowdine. J. Org. Chem., vol. 26, pp. 181-187, 1961.*
Tobinaga, S.: A review: Synthesis of alkaloids by oxidative phenol and nonphenol coupling reactions. Bioorg. Chem., vol. 4, pp. 110-125, 1975.*
Cahlikova, L. et al.: In vitro inhibitory effects of 8-O-demethylmartidine and Undulatine on Acetylcholinesterase and their predicted penetration across the blood-braon barrier. J. Natural products, vol. 78, pp. 1189-1192, 2015.*
Das, et al., Concise total syntheses of (+)- mesembrane and (+)-crinane. Organice & Biomolecular Chemistry. 2015. 13, 3585.
International Search Report and Written Opinion dated Sep. 11, 2017 for International PCT Patent Application No. PCT/US2017/029815.
PubChem. Compound summary for SID 53370983, Available Date: Sep. 12, 2008 [Retrieved on Jun. 13, 2007].
Henry, S. et al., 5,10b-Ethanophenanthridine amaryllidaceae alkaloids inspire the discovery of novel bicyclic ring systems with activity against drug resistant cancer cells. European Journal of Medicinal Chemistry.120 (2016) 313-328.
Hoover, John E., Remington's Pharmaceutical Sciences, Mack Publishing Co., Easton, Pennsylvania 1975.
Liberman, H.A. and Lachman, L., Eds., Pharmaceutical Dosage Forms, Marcel Decker, New York, N.Y., 1980.
Pharmaceutical Dosage Forms and Drug Delivery Systems, Seventh Ed. (Lippincott Williams & Wilkins 1999).
Remington: The Science and Practice of Pharmacy, Nineteenth Ed (Easton, Pa.: Mack Publishing Company, 1995).

* cited by examiner

*Primary Examiner* — Charanjit Aulakh
(74) *Attorney, Agent, or Firm* — Wilson Sonsini Goodrich & Rosati

(57) ABSTRACT

The present disclosure describes a method to treat conditions, including cancer, using compounds that can target resistant cancer cells. The compounds of the invention can decrease the rate of proliferation of drug-resistant cancer cells, such as glioma, lung cancer, and uterine sarcoma.

3 Claims, 9 Drawing Sheets

METHODS FOR TREATMENT OF RESISTANT CANCER

CROSS REFERENCE

This application claims the benefit of U.S. Provisional Application No. 62/329,393, filed Apr. 29, 2016; U.S. Provisional Application No. 62/341,120, filed May 25, 2016; and U.S. Provisional Application No. 62/364,891, filed Jul. 21, 2016, each of which are incorporated herein by reference in their entirety.

GOVERNMENT RIGHTS

The invention was made with government support under Grant Number P20GM103451 by the National Institute of General Medicinal Sciences. The government has certain rights in the invention.

BACKGROUND

Cancer, an uncontrolled proliferation of cells, is a multifactoral disease characterized by tumor formation, growth, and in some instances, metastasis. Current cancer therapies include chemotherapy and targeted therapies, which attempt to destroy cancer cells via apoptosis, necrosis, or proliferative inhibition. However, cancer cells can develop or harbor intrinsic resistance mechanisms through increased drug efflux, decreased cell permeability, and changes in enzyme activity or metabolic pathways to evade the effects of cancer therapies. The development of therapeutics that can overcome the drug-resistance mechanisms of cancer cells can assist in controlling the growth of drug-resistant tumors.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the disclosed invention provides a compound of the formula:

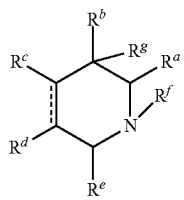

wherein:
- $R^a$ and $R^b$ together with the atoms to which $R^a$ and $R^b$ are bound form a ring;
- $R^c$ and $R^d$ together with the atoms to which $R^c$ and $R^d$ are bound form a ring;
- $R^e$ is alkyl, alkoxy, hydroxyl, or an amine group, any of which is substituted or unsubstituted, or H;
- $R^f$ and $R^g$ together with the atoms to which $R^f$ and $R^g$ are bound form a ring; and
- each ==== is independently a single bond or a double bond, or a pharmaceutically-acceptable salt thereof, wherein the compound is not:

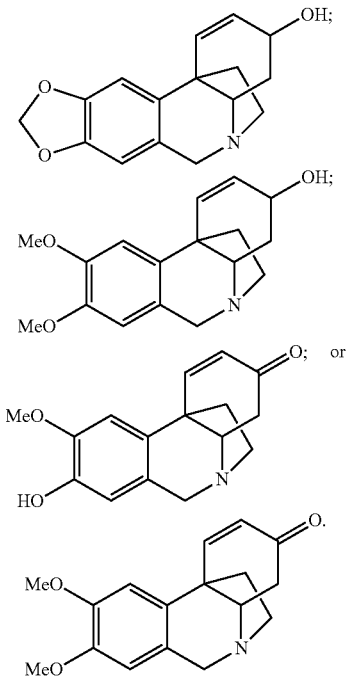

DETAILED DESCRIPTION

Figure 1:
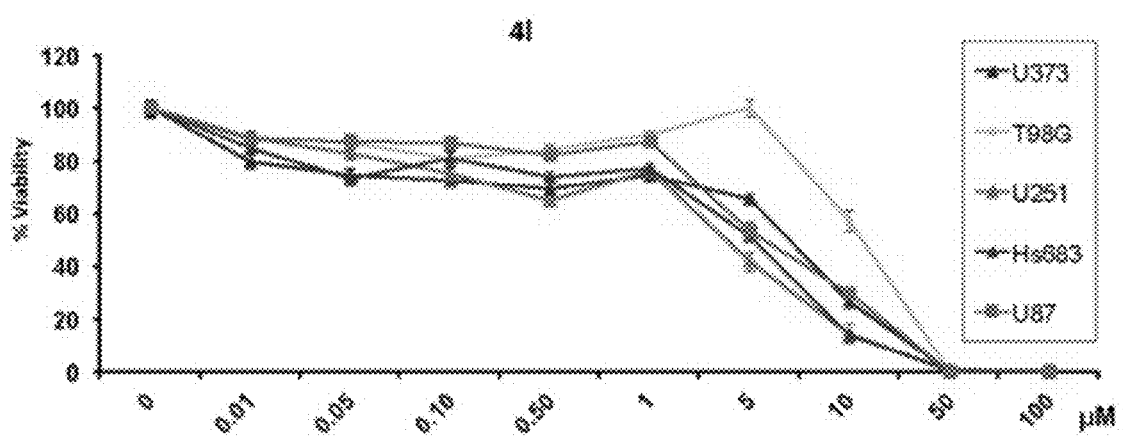
FIG. 1 depicts the growth curves of five GBM cell cultures treated with compound 4l.

Cancer.

The present invention provides methods for treating drug-resistant tumor cells using compounds described herein. The present compounds can decrease the rate of cellular proliferation in cancer cells, and target cancer cells that have resistance mechanisms against cell death and chemotherapy.

Cancer is a collection of related diseases characterized by the uncontrolled proliferation of cells, and has the potential to metastasize throughout the body. Cancer can be classified into five broad categories including, for example, carcinomas, sarcomas, lymphomas, leukemias, and adenomas. Carcinomas can arise from cells that cover internal and external parts of the body, such as the lung, breast, and colon. Sarcomas can arise from cells that are located in bone, cartilage, fat, connective tissue, muscle, and other supportive tissues. Lymphomas can arise in the lymph nodes and immune system tissues. Leukemias can arise in the bone marrow and accumulate in the bloodstream. Adenomas can arise in the thyroid, the pituitary gland, the adrenal gland, and other glandular tissues.

Although different cancers can develop in virtually any of the body's tissues, the basic processes that cause cancer can be similar in all forms of the disease. Cancer begins when a cell breaks free from the normal restraints of cell division and begins to grow and divide abnormally. Genetic mutations in the cell can preclude the ability of the cell to repair damaged DNA or initiate apoptosis, and can result in the uncontrolled growth and division of cells.

Oncogenes and tumor suppressor genes can regulate the proliferation of cells. Genetic mutations can affect oncogenes and tumor suppressors, potentially activating or suppressing activity abnormally, further facilitating uncontrolled cell division. Whereas oncogenes assist in cellular growth, tumor suppressor genes slow cell division by repairing damaged DNA and activating apoptosis. Cellular oncogenes that can be mutated in cancer include, for example, Cdk1, Cdk2, Cdk3, Cdk4, Cdk6, EGFR, PDGFR, VEGF, HER2, Raf kinase, K-Ras, and myc. Tumor suppressor genes that can be mutated in cancer include, for example, BRCA1, BRCA2, cyclin-dependent kinase inhibitor IC, Retinoblastoma protein (pRb), PTEN, p16, p27, p53, and p73.

Mechanisms of Drug-Resistance in Cancer Cells.

Apoptosis resistance is a hallmark of cancer because defects in apoptosis regulators invariably accompany tumorigenesis and sustain malignant progression. Because most standard chemotherapeutic agents work by inducing apoptosis in cancer cells, disruption in apoptosis during tumor evolution can promote intrinsic drug resistance and result in the failure of therapy.

Many cancer therapies target the apoptotic pathway to induce cell death in tumor cells. However, tumor cells can acquire resistance or harbor intrinsic resistance to these therapies by inducing mutations in the apoptotic pathway. The mechanisms of resistance to apoptosis can include, for example, alterations in death receptor pathways, changes in mitochondrial pathways, aberrant expression of inhibitor of apoptosis (IAP) proteins, and changes in DNA methylation patterns. Additional mechanisms of drug-resistance can include, for example, increased efflux of drugs from the cell, decreased cell permeability, and changes in the drug's binding site. Cancer cells can evade apoptosis through, for example, the suppression of p53 function, thereby suppressing expression of pro-apoptotic proteins.

The major death receptors in the cell include, for example, CD95 (APO-1/Fas), TNF receptor 1, and TRAIL. Tumor cells can downregulate the cell-surface expression of the death receptors or induce mutations in the genes encoding for the death receptors. Further, tumor cells can activate the expression of decoy receptors, thereby counteracting the effect of the death receptor ligands. Cancer cells can manipulate downstream targets of the death receptors by either upregulating the expression of, for example, anti-apoptotic proteins such as cFLIP, or downregulating the expression of, for example, pro-apoptotic proteins such as the caspases.

An increase in the permeability of the mitochondrial outer membrane can be an indicator of apoptosis in the cell, and is regulated by the Bcl-2 family of proteins. A resistant tumor cell can alter the expression of the Bcl-2 pro- and anti-apoptotic proteins to inhibit an increase in the permeability of the mitochondrial outer membrane, thereby inhibiting apoptosis. Pro-apoptotic members of the Bcl-2 family include, for example, Bax, BAD, Bak, and Bok. Anti-apoptotic members of the Bcl-2 family include, for example, Bcl-2, Bcl-xL, and Bcl-w. Resistant tumor cells can further deregulate the expression of IAP proteins including, for example, survivin, cIAP1, cIAP2, and XIAP.

The ATP binding cassette (ABC) family of transporters includes efflux pump transmembrane proteins found on the cell membrane. Efflux pumps can be used to transport, for example, toxins, metabolites, drugs, lipophilic cationic drugs, bile acids, fatty acids, and lipids. Efflux pumps can be specific for a single substrate or transport a range of structurally-similar or -dissimilar compounds, including chemotherapeutics. Increased expression of efflux pumps can be correlated with resistance to chemotherapeutics.

One type of cancer with intrinsic resistance against apoptosis induction is glioblastoma multiforme (GBM). GBM cells are highly resistant against many different apoptotic stimuli, and this resistance reduces the effectiveness of classic pro-apoptotic therapeutic approaches. GBM is characterized by a deregulated tumor genome containing opportunistic deletions of tumor suppressor genes and amplification or mutational hyper-activation of receptor tyrosine kinase receptors. These genetic changes result in enhanced survival pathways and systematic defects in the apoptotic machinery of GBM cells. As a result, GBM is associated with dismal prognoses, and GBM patients have a median survival expectancy of less than 14 months when treated with a standard protocol of surgical resection, radiotherapy, and chemotherapy with temozolomide (TMZ). Other apoptosis-resistant cancers include tumors of the lung, liver, stomach, esophagus, pancreas, and melanomas, which are all associated with dismal prognoses.

In addition to intrinsic resistance against chemotherapeutic agents, tumors can develop acquired resistance, in which tumors are initially susceptible to treatment and patients respond to chemotherapy, but then become resistant against a broad spectrum of structurally and mechanistically-diverse antitumor agents. This phenomenon is referred to as multi-drug resistance (MDR) and usually results from the upregulation of protein pumps, such as P-glycoprotein (P-gp), which leads to the reduction of drug concentrations in cancer cells. MDR is a cause of chemotherapy failure for widely used anticancer drugs, such as the vinca alkaloids or taxanes.

A compound of the invention can be tested on cell lines that harbor resistant mutations, or are programmed to become resistant to drugs or apoptosis. Cell lines that can be tested in a method of the invention include, for example, HEK-293T, H1299, HCT-116, MCF-7, U2OS, U251, U87, T98G, human GBM, A549 NSCLC, H1993, H2073, MES-SA, MES-SA/Dx5, HT1080, HeLa, Saos-2, IMR90, and MEF.

Compounds of the Invention.

The compounds disclosed herein can inhibit the proliferation of drug-resistant cancer cells in drug-resistant cancers, such as lung, liver, stomach, esophageal, pancreatic tumors, melanomas, and gliomas. At low concentrations, the compounds of the invention can slow cell replication and tumor growth.

The invention disclosed herein describes the generation of a collection of synthetic compounds based on the crinine-type 5,10b-ethanophenanthridine skeleton and their activities against drug-resistant cancer cells. The compounds of the invention exhibit single-digit micromolar activities and retain activity in a variety of drug-resistant cancer cell cultures. Also disclosed herein are new bicyclic ring systems that can be used as cancer drugs capable of overcoming resistance against chemotherapy.

Compounds of the invention include compounds of any of the following formulae:

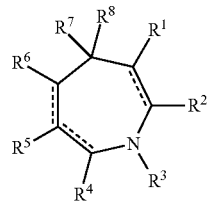

wherein:
each $R^1$, $R^2$, $R^3$, and $R^4$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted;

$R^5$ and $R^6$ together with the atoms to which $R^5$ and $R^6$ are bound form a ring that is substituted or unsubstituted;

$R^7$ and $R^8$ together with the atoms to which $R^7$ and $R^8$ are bound form a ring that is substituted or unsubstituted; and each ==== is independently a single bond or a double bond, or a pharmaceutically-acceptable salt thereof.

In some embodiments, $R^7$ and $R^8$ together with the atoms to which $R^7$ and $R^8$ are bound form a 5-, 6-, or 7-membered ring. In some embodiments, $R^7$ and $R^8$ together with the atoms to which $R^7$ and $R^8$ are bound form a 6-membered ring. In some embodiments, $R^7$ and $R^8$ together with the atoms to which $R^7$ and $R^8$ are bound form a 6-membered ring that is substituted with a carboxyl group.

In some embodiments, each $R^1$, $R^2$, $R^4$, $R^5$, and $R^6$ is independently hydrogen, halogen, hydroxyl, nitro, an acyl group, or an alkyl group. In some embodiments, each $R^1$, $R^2$, and $R^4$ is independently hydrogen.

In some embodiments, $R^5$ and $R^6$ together with the atoms to which $R^5$ and $R^6$ are bound form a 5- or 6-membered ring that is substituted. In some embodiments, $R^5$ and $R^6$ together with the atoms to which $R^5$ and $R^6$ are bound form a 6-membered ring that is substituted with alkoxy. In some embodiments, $R^5$ and $R^6$ together with the atoms to which $R^5$ and $R^6$ are bound form a ring that is substituted with OMe and OBn.

In some embodiments, the compound is of the formula:

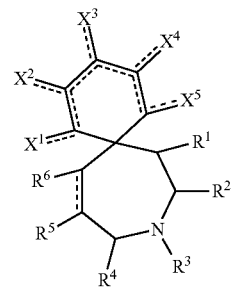

wherein each $X^1$, $X^2$, $X^3$, $X^4$, and $X^5$ is independently $CR^{13}R^{14}$, $CHR^{13}R^{14}$, $NR^{13}$, $OR^{13}$, $SR^{13}$, O, S, or absent; wherein each $R^{13}$ and $R^{14}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted.

In some embodiments, any one of $X^1$, $X^2$, $X^3$, $X^4$, and $X^5$ is O and the remaining of $X^1$, $X^2$, $X^3$, $X^4$, and $X^5$ are absent.

In some embodiments, $R^3$ is hydrogen, an acyl group, or alkyl. In some embodiments, $R^3$ is an acyl group. In some embodiments, $R^3$ is a formyl, acetyl, propionyl, butyryl, pivaloyl, trifluoroacetyl, trichloroacetyl, benzoyl, acryloyl, or propenoyl group.

In some embodiments, the compound is of the formula:

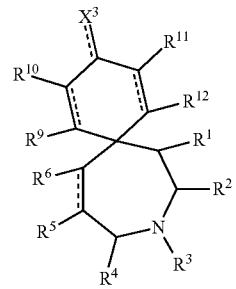

wherein:
each $R^9$, $R^{10}$, $R^{11}$, and $R^{12}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted;

$X^3$ is $CR^{13}R^{14}$, $CHR^{13}R^{14}$, $NR^{13}$, $OR^{13}$, $SR^{13}$, O, or S; and each $R^{13}$ and $R^{14}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted.

In some embodiments, each $R^9$, $R^{10}$, $R^{11}$, and $R^{12}$ is independently H, F, Cl, Br, I, OH, or alkyl. In some embodiments, each $R^9$, $R^{10}$, $R^{11}$, and $R^{12}$ is hydrogen.

In some embodiments, the compound is of the formula:

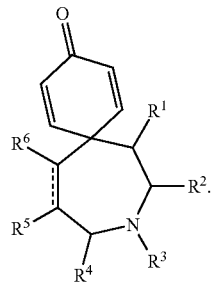

wherein:
each $R^1$, $R^2$, and $R^4$ is independently hydrogen, halogen, hydroxyl, sulfhydryl, nitro, alkyl, alkenyl, alkynyl, an alkoxy group, an ether group, an ester group, an amine group, or an amide group, any of which is substituted or unsubstituted;

$R^5$ and $R^6$ together with the atoms to which $R^5$ and $R^6$ are bound form a ring that is substituted or unsubstituted; and $R^3$ is alkyl, acyl, or an ester, any of which is substituted or unsubstituted.

In some embodiments, the compound is of the formula:

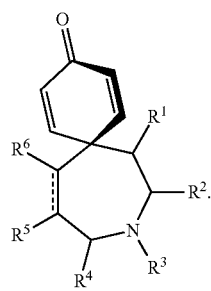

In some embodiments, each $R^1$, $R^2$, and $R^4$ is independently hydrogen, and $R^3$ is acyl. In some embodiments, $R^3$ is $C(O)CF_3$.

In some embodiments, $R^5$ and $R^6$ together with the atoms to which $R^5$ and $R^6$ are bound form a 5-membered ring, wherein the 5-membered ring is substituted or unsubstituted. In some embodiments, $R^5$ and $R^6$ are bound to a moiety of the formula:

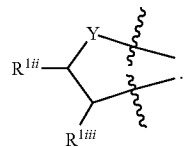

In some embodiments, the compound is of the formula:

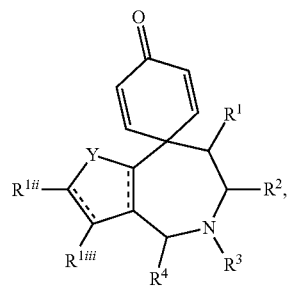

wherein:
Y is $N(R^{1i})$, S, or O;
$R^{1i}$ is hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted; and
each $R^{1ii}$ and $R^{1iii}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted; or
$R^{1ii}$ and $R^{1iii}$ together with the atoms to which $R^{1ii}$ and $R^{1iii}$ are bound form a ring that is substituted or unsubstituted.

In some embodiments, the compound is of the formula:

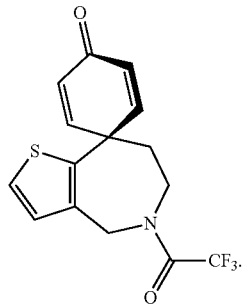

In some embodiments, the compound is of the formula:

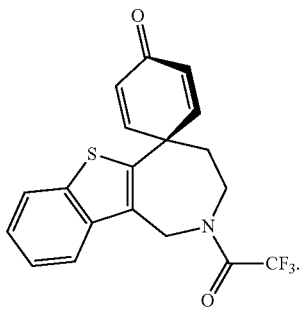

In some embodiments, $R^5$ and $R^6$ together with the atoms to which $R^5$ and $R^6$ are bound form a 6-membered ring, wherein the 6-membered ring is substituted or unsubstituted. In some embodiments, $R^5$ and $R^6$ are bound to a moiety of the formula:

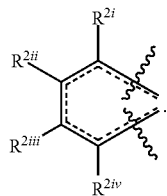

In some embodiments, the compound is of the formula:

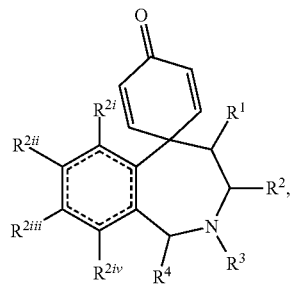

wherein:
each $R^{2i}$, $R^{2ii}$, $R^{2iii}$, and $R^{2iv}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted;

each $R^{2iii}$ and $R^{2iv}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted, and $R^{2i}$ and $R^{2ii}$ together with the atoms to which $R^{2i}$ and $R^{2ii}$ are bound form a ring that is substituted or unsubstituted;

each $R^{2i}$ and $R^{2iv}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted; and $R^{2ii}$ and $R^{2iii}$ together with the atoms to which $R^{2ii}$ and $R^{2iii}$ are bound form a ring that is substituted or unsubstituted; or each $R^{2i}$ and $R^{2ii}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted; and $R^{2iii}$ and $R^{2iv}$ together with the atoms to which $R^{2iii}$ and $R^{2iv}$ are bound form a ring that is substituted or unsubstituted.

In some embodiments, each ==== is independently chosen to create an aromatic system.

In some embodiments, $R^3$ is an ester. In some embodiments, $R^3$ is $C(O)CF_3$.

In some embodiments, each $R^{2ii}$ and $R^{2iii}$ is an alkoxy group. In some embodiments, each $R^{2ii}$ and $R^{2iii}$ is OMe. In some embodiments, each $R^{2ii}$ and $R^{2iii}$ is OBn. In some embodiments, each $R^{2ii}$ is OMe and $R^{2iii}$ is OBn. In some embodiments, each $R^{2ii}$ is OBn and $R^{2iii}$ is OMe.

In some embodiments, $R^{2ii}$ and $R^{2iii}$ together with the atoms to which $R^{2ii}$ and $R^{2iii}$ are bound form a ring. In some embodiments, $R^{2ii}$ and $R^{2iii}$ together with the atoms to which $R^{2ii}$ and $R^{2iii}$ are bound form a 5-membered ring. In some embodiments, $R^{2ii}$ and $R^{2iii}$ together with the atoms to which $R^{2ii}$ and $R^{2iii}$ are bound form a 6-membered ring. In some embodiments, $R^{2iii}$ and $R^{2iv}$ together with the atoms to which $R^{2iii}$ and $R^{2iv}$ are bound form a ring. In some embodiments, $R^{2iii}$ and $R^{2iv}$ together with the atoms to which $R^{2iii}$ and $R^{2iv}$ are bound form a 5-membered ring. In some embodiments, $R^{2iii}$ and $R^{2iv}$ together with the atoms to which $R^{2iii}$ and $R^{2iv}$ are bound form a 6-membered ring.

In some embodiments, the compound is of the formula:

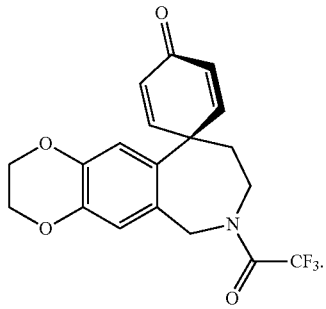

In some embodiments, the compound is of the formula:

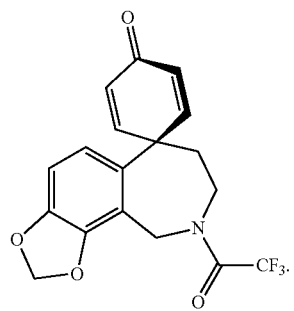

Compounds of the invention also include compounds of any of the following formulae:

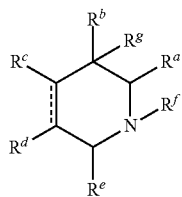

wherein $R^a$ and $R^b$ together with the atoms to which $R^a$ and $R^b$ are bound form a ring; $R^c$ and $R^d$ together with the atoms to which $R^c$ and $R^d$ are bound form a ring; $R^e$ is alkyl, alkoxy, hydroxyl, or an amine group, any of which is substituted or unsubstituted, or H; $R^f$ and $R^g$ together with the atoms to which $R^f$ and $R^g$ are bound form a ring; and each ==== is independently a single bond or a double bond, or a pharmaceutically-acceptable salt thereof, wherein the compound is not:

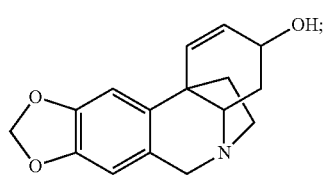

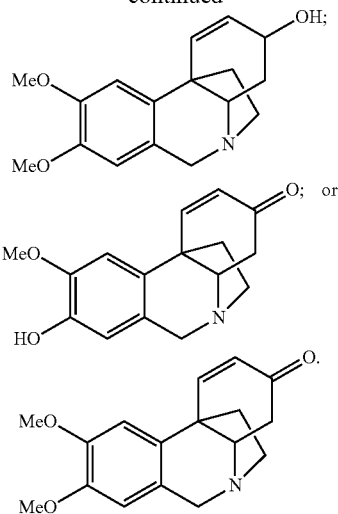

In some embodiments, the compound is of the formula:

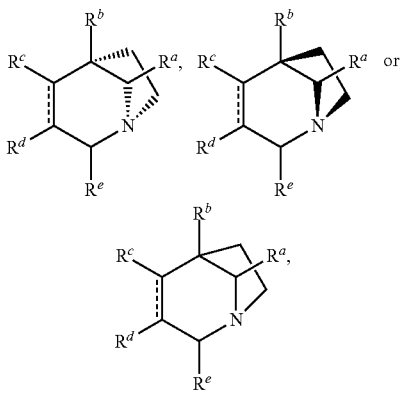

wherein $R^a$ and $R^b$ together with the atoms to which $R^1$ and $R^2$ are bound form a ring; $R^c$ and $R^d$ together with the atoms to which $R^c$ and $R^d$ are bound form a ring; $R^e$ is alkyl, alkoxy, hydroxyl, or an amine group, any of which is substituted or unsubstituted, or H; and each ==== is independently a single bond or a double bond, or a pharmaceutically-acceptable salt thereof.

In some embodiments, ==== is a double bond.

In some embodiments, $R^a$ and $R^b$ together with the atoms to which $R^a$ and $R^b$ are bound form a ring, for example, a 4-, 5-, 6-, 7-, 8-, 9-, 10-, 11-, or 12-membered ring, wherein the ring is substituted or unsubstituted. In some embodiments, $R^a$ and $R^b$ together with the atoms to which $R^a$ and $R^b$ are bound form a 6- or 7-membered ring, wherein the 6- or 7-membered ring is substituted or unsubstituted. In some embodiments, $R^a$ and $R^b$ together with the atoms to which $R^a$ and $R^b$ are bound form a ring, for example, a 4-, 5-, 6-, 7-, 8-, 9-, 10-, 11-, or 12-membered carbocycle having 3 sp$^2$ carbon atoms, wherein the carbocycle is substituted or unsubstituted. In some embodiments, $R^a$ and $R^b$ together with the atoms to which $R^a$ and $R^b$ are bound form a 6- or 7-membered carbocycle having 3 sp$^2$ carbon atoms, wherein the 6- or 7-membered carbocycle is substituted or unsubstituted. In some embodiments, $R^a$ and $R^b$ together with the atoms to which $R^a$ and $R^b$ are bound form a ring, for example, a 4-, 5-, 6-, 7-, 8-, 9-, 10-, 11-, or 12-membered heterocycle having 3 sp² carbon atoms, wherein the heterocycle is substituted or unsubstituted. In some embodiments, R^a and R^b together with the atoms to which R^a and R^b are bound form a 7-membered heterocycle having 3 sp² carbon atoms, wherein the 7-membered heterocycle is substituted or unsubstituted.

In some embodiments, R^a and R^b together with the atoms to which R^a and R^b are bound form a ring, for example, a 4-, 5-, 6-, 7-, 8-, 9-, 10-, or 11-membered ring having 2 sp² carbon atoms, wherein the ring is substituted with a hydroxyl group. In some embodiments, R^a and R^b together with the atoms to which R^a and R^b are bound form a 6- or 7-membered ring having 2 sp² carbon atoms, wherein the 6- or 7-membered ring is substituted with a hydroxyl group. In some embodiments, the ring formed by R^a and R^b together with the atoms to which R^a and R^b are bound is substituted with a hydroxyl group. In some embodiments, the ring formed by R^a and R^b together with the atoms to which R^a and R^b are bound is substituted with a halogen. In some embodiments, the ring formed by R^a and R^b together with the atoms to which R^a and R^b are bound is substituted with bromine.

In some embodiments, R^c and R^d together with the atoms to which R^c and R^d are bound form an aryl ring that is substituted or unsubstituted. In some embodiments, R^c and R^d together with the atoms to which R^c and R^d are bound form an aryl ring that is substituted or unsubstituted. In some embodiments, R^c and R^d together with the atoms to which R^c and R^d are bound form a heteroaryl ring that is substituted or unsubstituted. In some embodiments, R^c and R^d together with the atoms to which R^c and R^d are bound form a heterocyclic ring that is substituted or unsubstituted. In some embodiments, R^c and R^d together with the atoms to which R^c and R^d are bound form a bicyclic ring that is substituted or unsubstituted.

In some embodiments, R^c and R^d together with the atoms to which R^c and R^d are bound form a benzo group that is substituted or unsubstituted. In some embodiments, the benzo group is substituted with one benzyl group. In some embodiments, R^c and R^d together with the atoms to which R^c and R^d are bound form a benzothiophene group that is substituted or unsubstituted.

In some embodiments, R^e is H.

In some embodiments, the compound is of the formula:

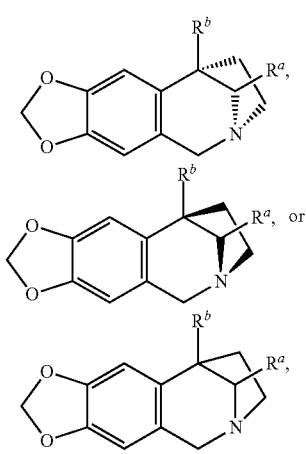

wherein R¹ and R² together with the atoms to which R¹ and R² are bound form a ring.

In some embodiments, the compound is of the formula:

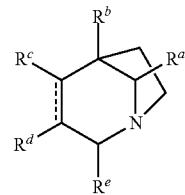

wherein R¹ and R² together with the atoms to which R¹ and R² are bound form a ring; R³ and R⁴ together with the atoms to which R³ and R⁴ are bound form a carbocycle that is substituted or unsubstituted, and R⁵ is H; and each ==== is independently a single bond or a double bond.

In some embodiments, the compound is of the formula:

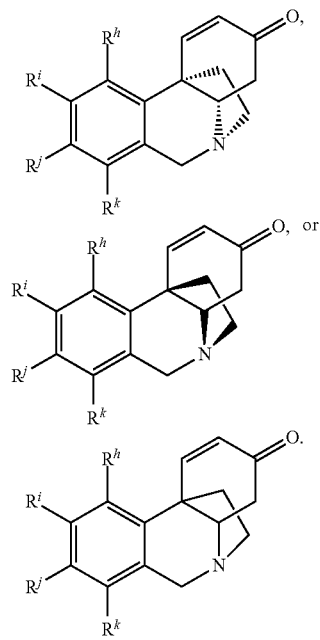

wherein each R^h, R^i, R^j, and R^k is independently H, halo-, O(alkyl), or O(aryl), or any of R^h and R^i, R^j and R^k, and R^i and R^k together with the atoms to which R^h and R^i, R^i and R^j, or R^j and R^k are bound form a substituted or unsubstituted ring. In some embodiments, R^i is OMe and R^j is OBn.

In some embodiments, the compound is of the formula:

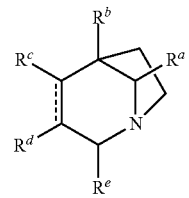

wherein R^a and R^b together with the atoms to which R^a and R^b are bound form a ring; R^c and R^d together with the atoms to which R^c and R^d are bound form a heterocycle that is substituted or unsubstituted; R^e is H; and each ==== is independently a single bond or a double bond.

Compounds herein can include any stereoisomers, enantiomers, diastereomers, mixtures, racemates, atropisomers, and tautomers thereof.

In some embodiments, the compound is of the formula:

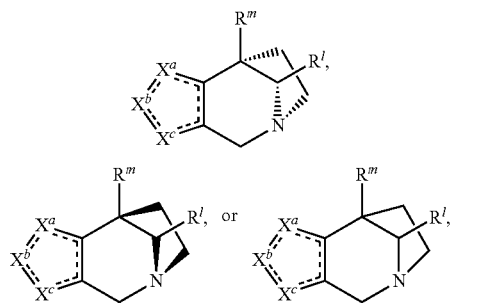

wherein $R^t$ and $R^m$ together with the atoms to which $R^t$ and $R^m$ are bound form a ring that is substituted or unsubstituted; $X^a$ is S, O, or NH; $X^b$ is S, O, or C(R″); $X^c$ is S, O, or C(R°); and each R″ and R° is H, or R″ and R° together with the atoms to which R″ and R° are bound form a substituted or unsubstituted ring, or a pharmaceutically-acceptable salt thereof. In some embodiments, $X^a$ is S, $X^b$ is C(R″), $X^c$ is C(R°), and R″ and R° together with the atoms to which R″ and R° are bound form a benzo group. In some embodiments, R″ and R° together with the atoms to which R″ and R° are bound form a benzo group that is substituted or unsubstituted.

In some embodiments, a compound of the invention is one of the following:

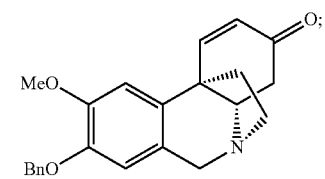

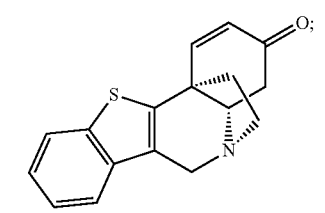

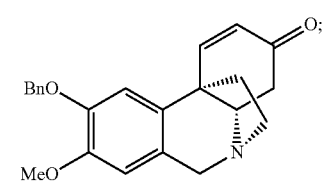

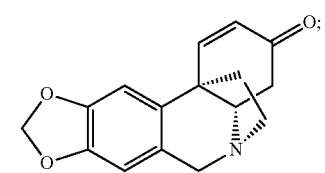

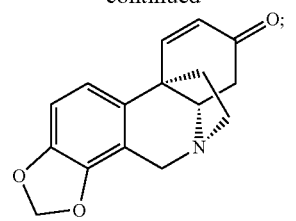

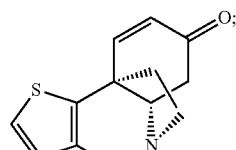

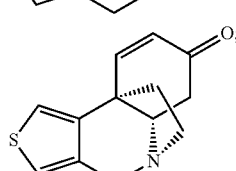

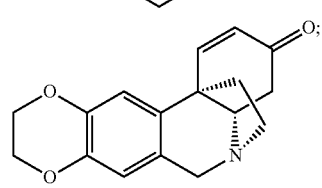

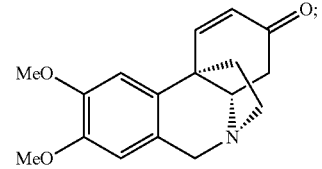

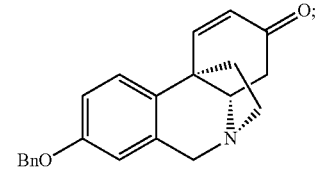

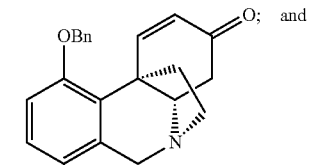

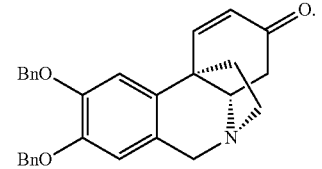

In some embodiments, a compound of the invention is one of the following:

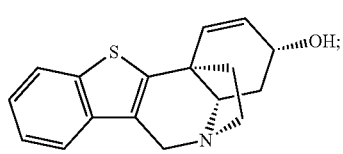

-continued
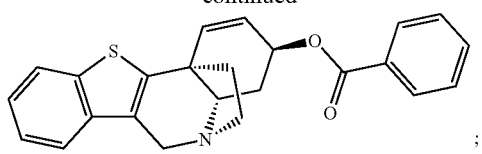;
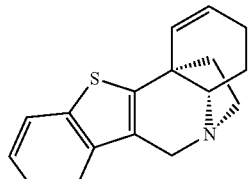;
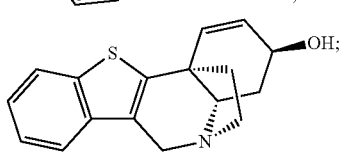;
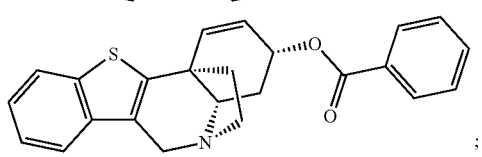;
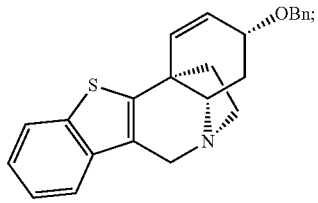;
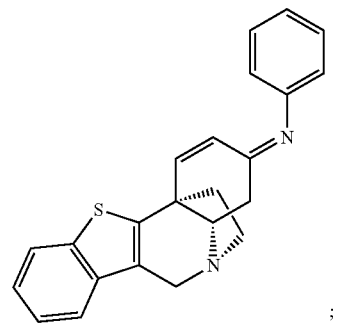;
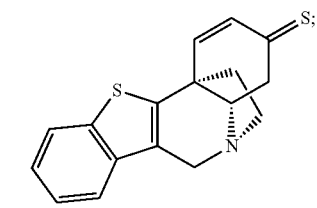;
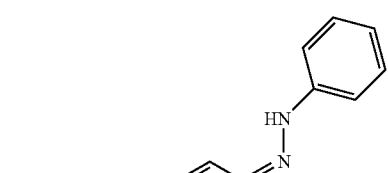;
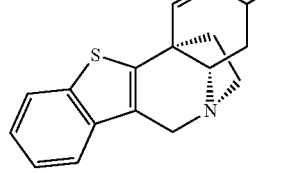;
-continued
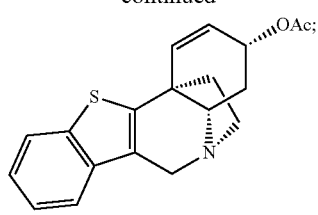;
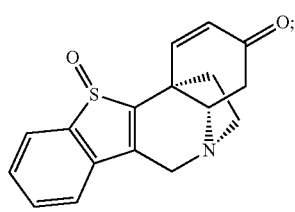;
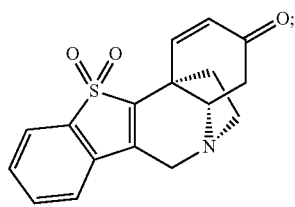;
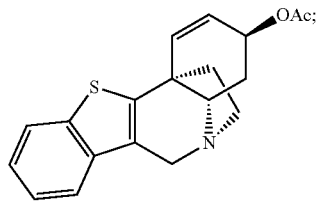;
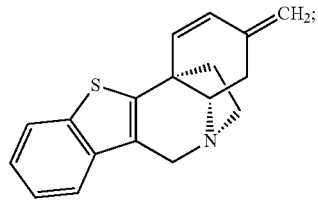;
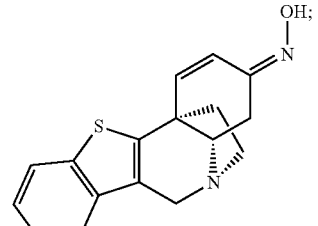;
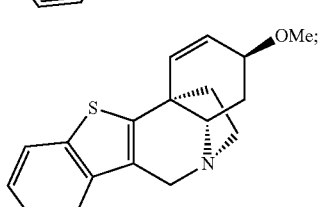;
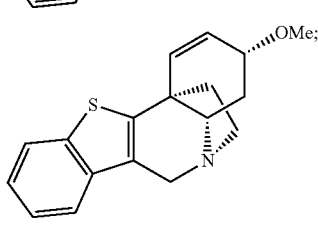;

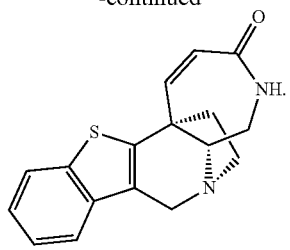

Optional Substituents for Chemical Groups.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, and ester groups.

Non-limiting examples of alkyl and alkylene groups include straight, branched, and cyclic alkyl and alkylene groups. An alkyl or alkylene group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of cyclic alkyl groups include cyclopropyl, cyclobutyl, cyclopentyl, cyclohexyl, cycloheptlyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl.

An aryloxy group can be, for example, an oxygen atom substituted with any aryl group, such as phenoxy.

An aralkyl group can be, for example, any alkyl group substituted with any aryl group, such as benzyl.

An arylalkoxy group can be, for example, an oxygen atom substituted with any aralkyl group, such as benzyloxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group. A non-limiting example of an acyloxy group, or an ester group, is acetate.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

Pharmaceutically-Acceptable Salts.

The invention provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Purity of Compounds of the Invention.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

In some embodiments, compounds of the invention can be applied topically to the skin, or a body cavity, for example, oral, vaginal, bladder, cranial, spinal, thoracic, or pelvic cavity of a subject. In some embodiments, the compounds of the invention can be applied to an accessible body cavity.

Compounds of the invention can increase cell death in a cell by, for example, about 2-fold, about 3-fold, about 4-fold, about 5-fold, about 6-fold, about 7-fold, about 8-fold, about 9-fold, about 10-fold, about 11-fold, about 12-fold, about 13-fold, about 14-fold, about 15-fold, about 16-fold, about 17-fold, about 18-fold, about 19-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, about 100-fold, about 110-fold, about 120-fold, about 130-fold, about 140-fold, about 150-fold, about 160-fold, about 170-fold, about 180-fold, about 190-fold, about 200-fold, about 250-fold, about 300-fold, about 350-fold, about 400-fold, about 450-fold, about 500-fold, about 550-fold, about 600-fold, about 650-fold, about 700-fold, about 750-fold, about 800-fold, about 850-fold, about 900-fold, about 950-fold, about 1000-fold, about 1500-fold, or about 2000-fold greater than when the cell is not exposed to the compound.

A compound herein can bind a cellular target that is associated with a drug resistance mechanism, for example, an efflux pump. The binding can cause a decrease in the efficacy of the drug resistance mechanism, thereby increasing the efficacy of the compound within the cell. A compound herein can cause a decrease in efficacy of a drug resistance mechanism that is, for example, about 2-fold, about 3-fold, about 4-fold, about 5-fold, about 6-fold, about 7-fold, about 8-fold, about 9-fold, about 10-fold, about 11-fold, about 12-fold, about 13-fold, about 14-fold, about 15-fold, about 16-fold, about 17-fold, about 18-fold, about 19-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, about 100-fold, about 110-fold, about 120-fold, about 130-fold, about 140-fold, about 150-fold, about 160-fold, about 170-fold, about 180-fold, about 190-fold, about 200-fold, about 250-fold, about 300-fold, about 350-fold, about 400-fold, about 450-fold, about 500-fold, about 550-fold, about 600-fold, about 650-fold, about 700-fold, about 750-fold, about 800-fold, about 850-fold, about 900-fold, about 950-fold, about 1000-fold, about 1500-fold, or about 2000-fold in comparison to the efficacy of the drug resistance mechanism in a cell that has not been treated with the compound.

Compounds of the invention can display $GI_{50}$ values that are, for example, about 0.1 nM, about 0.2 nM, about 0.3 nM, about 0.4 nM, about 0.5 nM, about 0.6 nM, about 0.7 nM, about 0.8 nM, about 0.9 nM, about 1 nM, about 1.5 nM, about 2 nM, about 2.5 nM, about 3 nM, about 3.5 nM, about 4 nM, about 4.5 nM, about 5 nM, about 5.5 nM, about 6 nM, about 6.5 nM, about 7 nM, about 7.5 nM, about 8 nM, about 8.5 nM, about 9 nM, about 9.5 nM, about 10 nM, about 15 nM, about 20 nM, about 25 nM, about 30 nM, about 35 nM, about 40 nM, about 45 nM, about 50 nM, about 60 nM, about 70 nM, about 80 nM, about 90 nM, about 100 nM, about 110 nM, about 120 nM, about 130 nM, about 140 nM, about 150 nM, about 200 nM, about 250 nM, about 300 nM, about 350 nM, about 400 nM, about 450 nM, about 500 nm, about 600 nM, about 700 nM, about 800 nM, about 900 nM, about 1 µM, about 1.5 µM, about 2 µM, about 2.5 µM, about 3 µM, about 3.5 µM, about 4 µM, about 4.5 µM, about 5 µM, about 6 µM, about 7 µM, about 8 µM, about 9 µM, about 10 µM, about 15 µM, about 20 µM, about 25 µM, about 30 µM, about 35 µM, about 40 µM, about 45 µM, about 50 µM, about 60 µM, about 70 µM, about 80 µM, about 90 µM, about 100 µM, about 150 µM, about 200 µM, about 300 µM, about 400 µM, about 500 µM, about 600 µM, about 700 µM, about 800 µM, about 900 µM, or about 1 mM.

Pharmaceutical Compositions of the Invention.

A pharmaceutical composition of the invention can be used, for example, before, during, or after treatment of a subject with another pharmaceutical agent.

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N,N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the invention is administered in combination with, before, or after an antibiotic. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 µg, about 10 µg, about 100 µg, about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dose can be expressed in terms of an amount of the drug divided by the mass of the subject, for example, milligrams of drug per kilograms of subject body mass. In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

Diseases.

In some embodiments, compounds of the invention can be used to treat cancer in a subject. A compound of the invention can, for example, slow the proliferation of cancer cell lines, or kill cancer cells. Non-limiting examples of cancer that can be treated by a compound of the invention include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

Subjects can be, for example, elderly adults, adults, adolescents, pre-adolescents, children, toddlers, infants, and non-human animals. In some embodiments, a subject is a patient. Non-human animal subjects can be, for example, a mouse, rat, a chicken, a rabbit, a dog, a cat, or a cow.

EXAMPLES

Example 1: Synthesis of Compounds of the Invention

All reagents, solvents, and catalysts were purchased from commercial sources (i.e., Acros Organics™ and Sigma-Aldrich™) and used without purification. All reactions were performed in oven-dried flasks open to the atmosphere or under nitrogen or argon and monitored by thin layer chromatography (TLC) on TLC precoated (250 μm) silica gel 60 F254 glass-backed plates (EMD Chemicals Inc.™). Visualization was accomplished with UV light. Flash column chromatography was performed on silica gel (32-63 μm, 60 Å pore size). $^1$H and $^{13}$C NMR spectra were recorded on a Bruker™ 400 spectrometer. Chemical shifts (δ) are reported in ppm relative to the TMS internal standard. Abbreviations are as follows: s (singlet), d (doublet), t (triplet), q (quartet), m (multiplet).

SCHEME 1 shows the synthetic steps used to prepare a library of the crinine analogues of the invention. The 5,10b-ethanophenanthridine ring system was used to generate compounds 5a-l.

TABLE 1 shows compounds 1a-l, compounds 2a-l, compounds 3a-l, compounds 4a-l, and compounds 5a-l of the invention. Compounds 1a-l, 2a-l, 3a-l, and 4a-l are synthetic intermediates that were generated in the process of synthesizing compounds 5a-l.

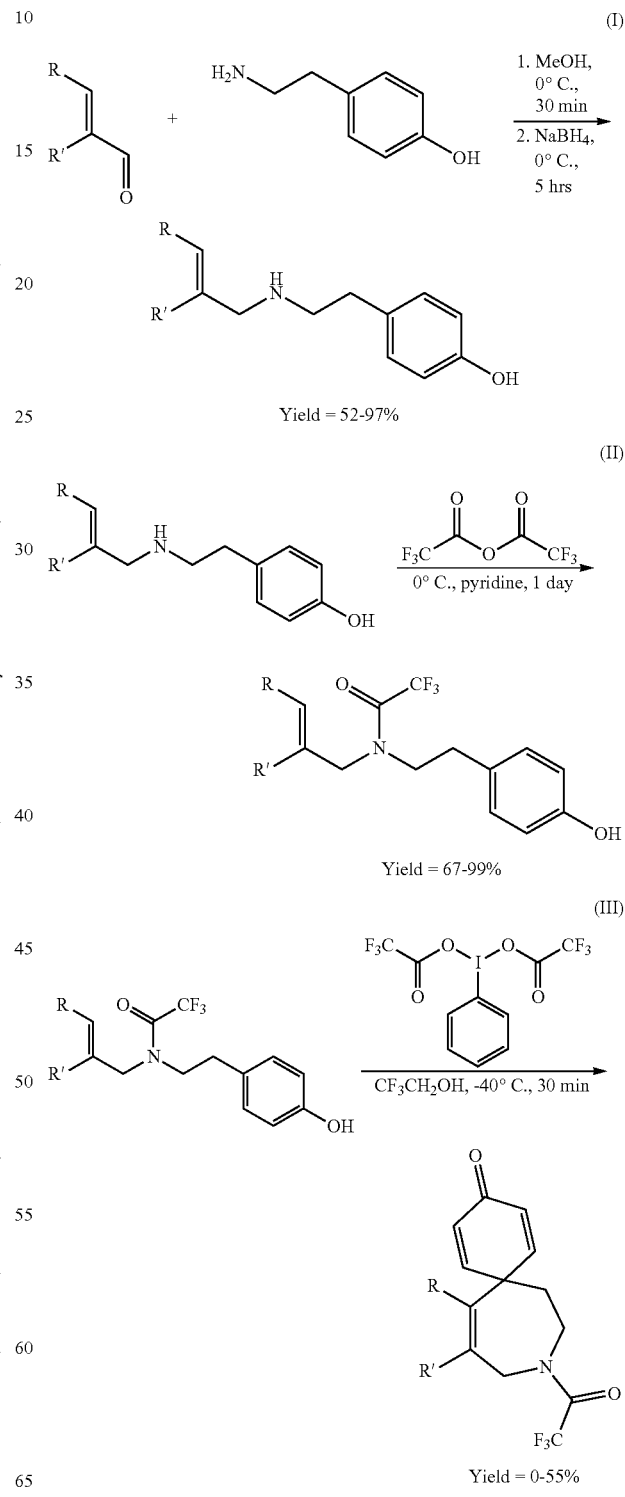

31
-continued

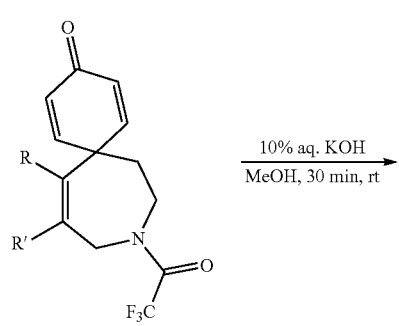

(IV)

32
-continued

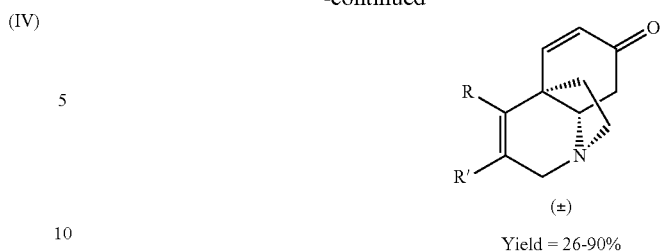

(±)

Yield = 26-90%

TABLE 1

| | Compound 1 | Compound 2 | Compound 3 |
|---|---|---|---|
| a | (benzo[d][1,3]dioxol-5-yl)-CHO | benzo[d][1,3]dioxol-5-ylmethyl-NH-CH2CH2-(4-hydroxyphenyl), 75% | N-(benzo[d][1,3]dioxol-5-ylmethyl)-N-(4-hydroxyphenethyl)-2,2,2-trifluoroacetamide, 94% |
| b | 3,4-dimethoxybenzaldehyde | 3,4-dimethoxybenzyl-NH-CH2CH2-(4-hydroxyphenyl), 82% | N-(3,4-dimethoxybenzyl)-N-(4-hydroxyphenethyl)-2,2,2-trifluoroacetamide, 77% |
| c | 2,3-dihydrobenzo[b][1,4]dioxine-6-carbaldehyde | (2,3-dihydrobenzo[b][1,4]dioxin-6-yl)methyl-NH-CH2CH2-(4-hydroxyphenyl), 95% | N-((2,3-dihydrobenzo[b][1,4]dioxin-6-yl)methyl)-N-(4-hydroxyphenethyl)-2,2,2-trifluoroacetamide, 82% |

TABLE 1-continued
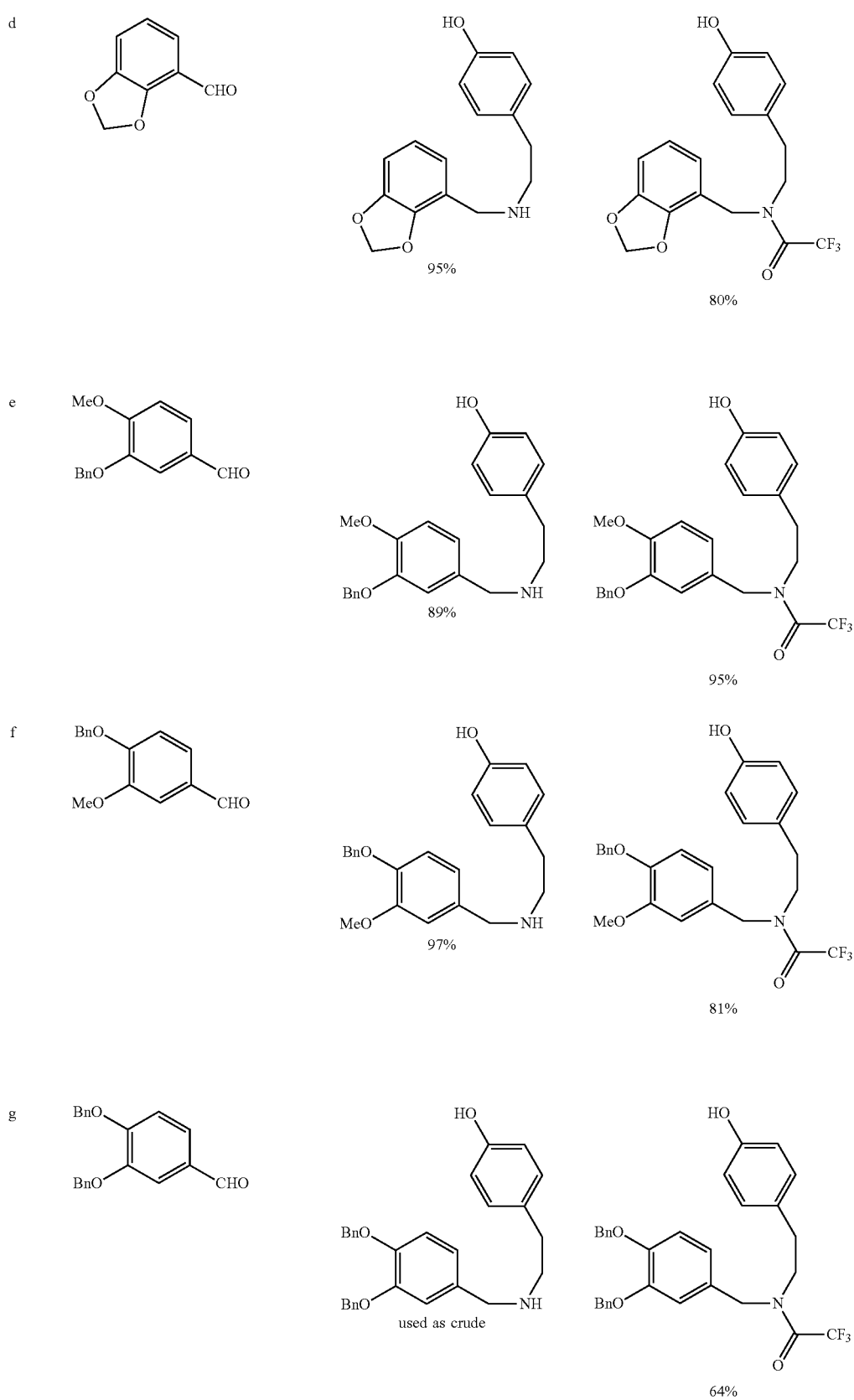

TABLE 1-continued
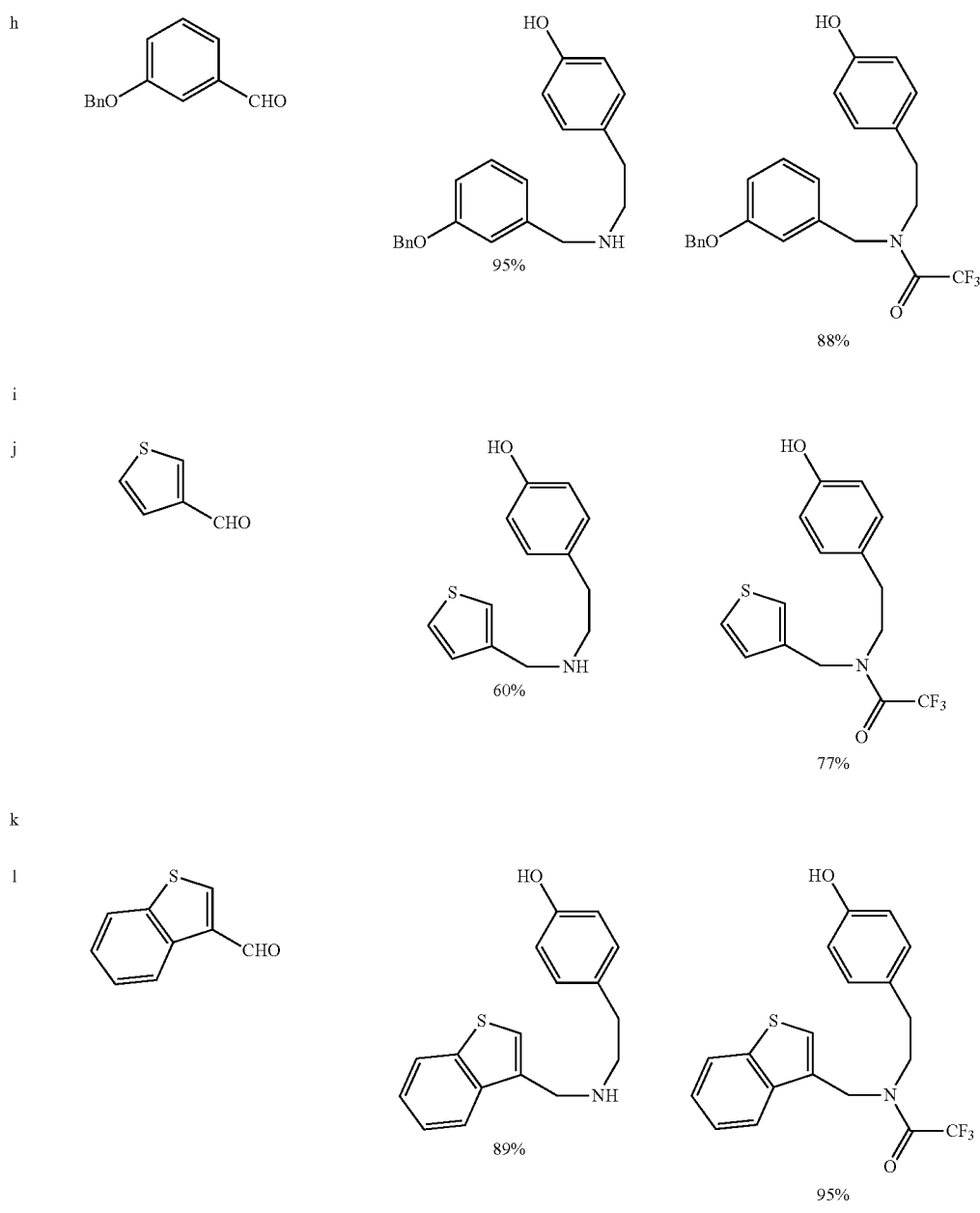
| | Compound 4 | Compound 5 |
|---|---|---|
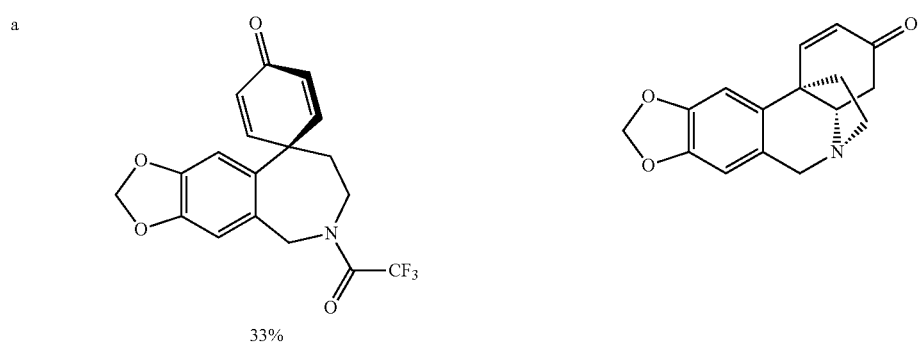

TABLE 1-continued
b 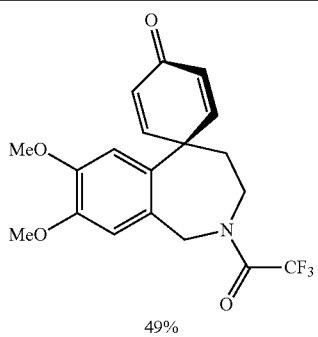
49%
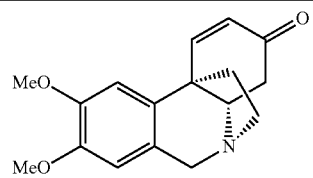
c 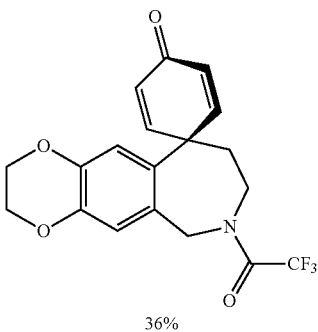
36%
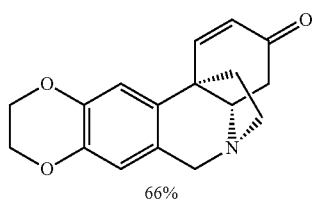
66%
d 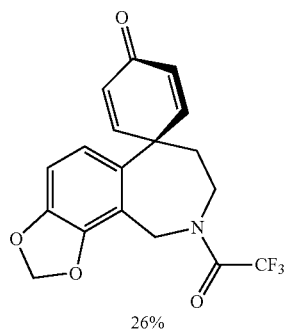
26%
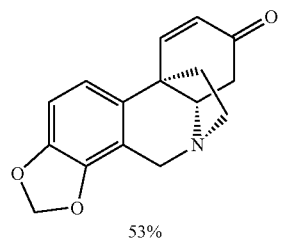
53%
e 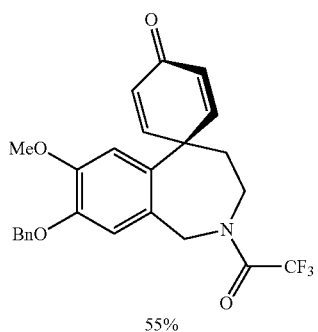
55%
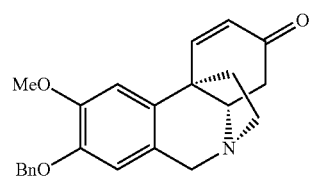
f 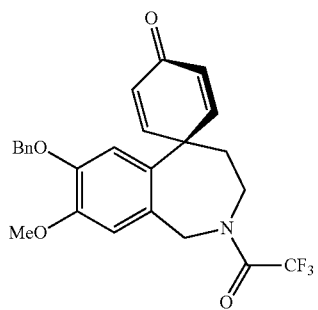
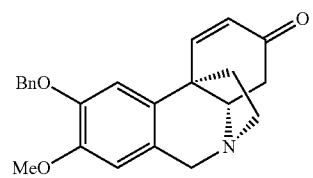

TABLE 1-continued
41%
g 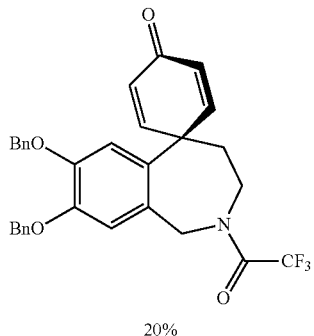 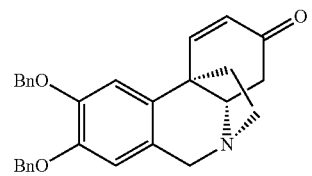
20%
h 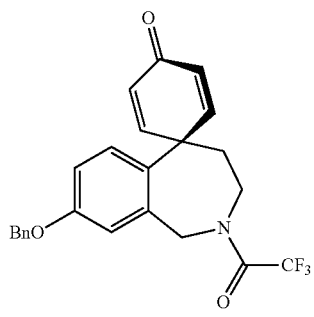 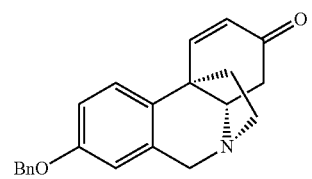 [SMILES: O=C1C=C[C@]23CC[N@](Cc4cc(OCc5ccccc5)ccc42)[C@H]3C1]
21%
i 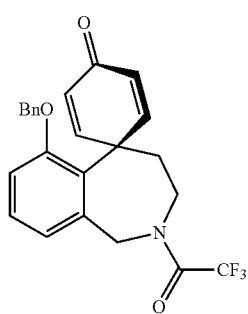 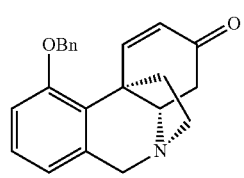 [SMILES: O=C1C=C[C@]23CC[N@](Cc4cccc(OCc5ccccc5)c42)[C@H]3C1]
11%
j 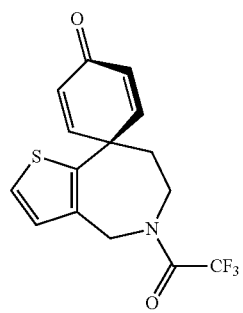 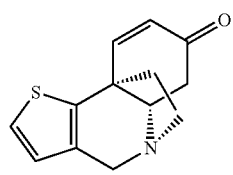
isolated as mixture with 4k TABLE 1-continued

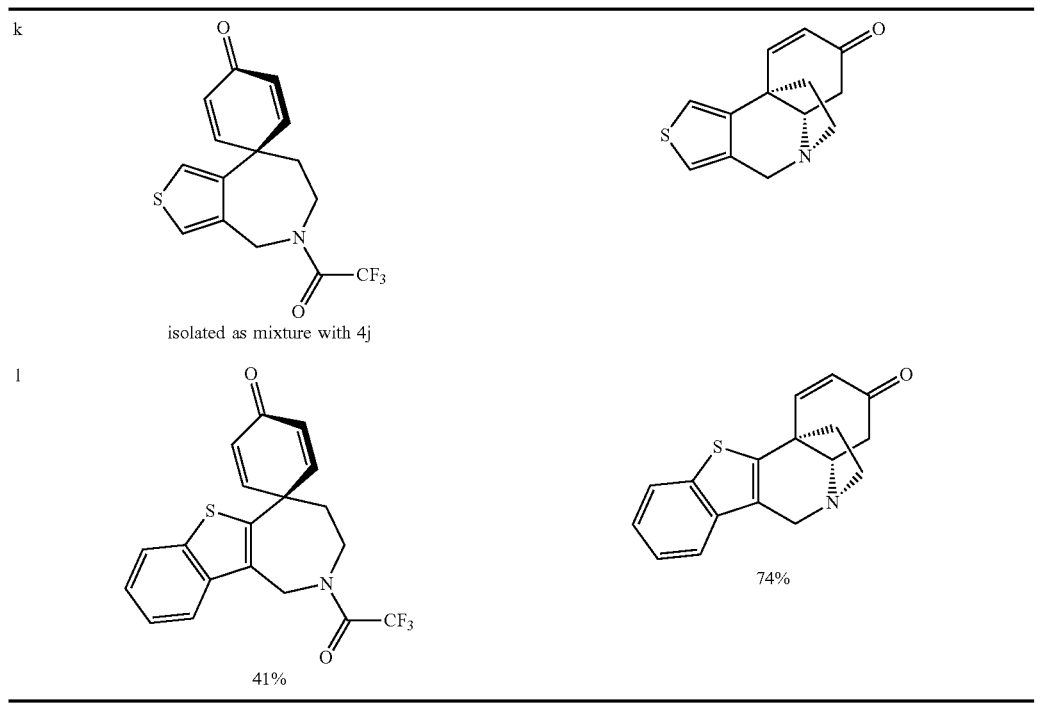

k — isolated as mixture with 4j l — 41% / 74%

Aromatic aldehydes 1a-l were reacted with tyramine to form imines, which were reduced with sodium borohydrate to the corresponding amines 2a-l (SCHEME 2). Intermediates 2a-l were protected as trifluoroacetamides 3a-l and were then subjected to oxidative cyclization promoted with phenyliodine (III) bis(trifluoroacetate) (PIFA) in 2,2,2-trifluoroethanol to afford spirodienones 4a-l. Spirodienones 4a-l were subsequently treated with KOH in a mixture of methanol and water at room temperature to afford Compounds 5a-l.

SCHEME 2

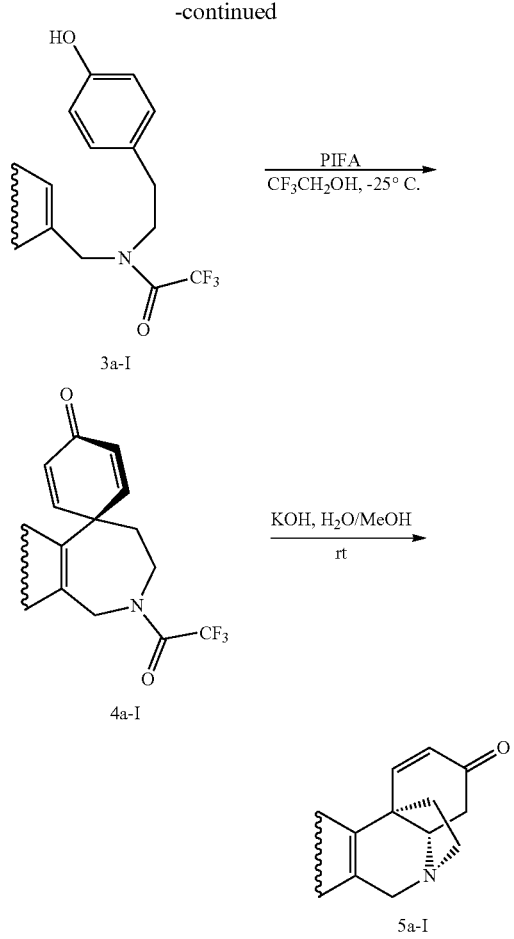

All compounds in TABLE 1 underwent highly regioselective oxidative cyclization of compounds 3 to afford compounds 4, with the exception of substrates 3h and 3j, where mixtures of isomeric spirodienones 4h/i and 4j/k were obtained. The structures of these synthesized compounds and reaction yields are shown in TABLE 1.

Example 2: Synthesis of Compounds 2a-h, 2j, and 2l

Reaction I: To a flask containing 4.1 mmol of a selected aromatic aldehyde in 10.2 mL of methanol at 0° C. was added 0.7452 g (5.4 mmol) of tyramine. The solution was stirred for 45 min, and 0.1808 g (4.8 mmol) of sodium borohydride was added. The solution was stirred for 4.5 h, at which point 0.1679 g (4.4 mmol) of additional sodium borohydride was added. This mixture was stirred overnight, and the formed precipitate was collected via vacuum filtration. No further purification was required at this stage.

Compound 2c: 95%; $^1$H NMR (CDCl$_3$): δ 6.96 (d, J=8.0 Hz, 2H), 6.78-6.66 (m, 5H), 4.22 (m, 4H), 3.69 (broad s, 2H), 2.84 (t, J=7.1 Hz, 2H), 2.72 (t, J=7.1 Hz, 2H); $^{13}$C NMR (CDCl$_3$): δ 154.6, 143.4, 142.6, 132.9, 131.1, 129.8, 121.3, 117.2, 117.1, 115.6, 64.3, 53.1, 50.2, 35.0; HRMS calc'd for C$_{17}$H$_{20}$NO$_3$ (M+H)$^+$: 286.1438, found 286.1441.

Compound 2d: 95%; $^1$H NMR (CDCl$_3$): δ 6.95 (d, J=8.4 Hz, 2H), 6.89-6.65 (m, 5H), 5.81 (s, 2H), 5.46 (broad s, 1H), 3.79 (s, 2H), 2.85 (t, J=7.1 Hz, 2H), 2.74 (t, J=7.1 Hz, 2H). $^{13}$C NMR (CDCl$_3$): δ 156.1, 147.3, 145.5, 129.9, 122.3, 121.6, 120.6, 116.3, 116.1, 107.8, 100.8, 50.0, 47.8, 34.7. HRMS calc'd for C$_{16}$H$_{18}$NO$_3$ (M+H)$^+$: 272.1281, found 272.1286.

Compound 2f: 97%; $^1$H NMR (CDCl$_3$): 7.40 (d, J=7.2 Hz, 2H), 7.33 (t, J=7.6 Hz, 2H), 7.28 (d, J=7.2 Hz, 1H), 7.01 (d, J=8.4 Hz, 2H), 6.82 (d, J=3.6 Hz, 1H), 6.78 (d, J=8.2 Hz, 1H), 6.70-6.68 (m, 3H), 5.11 (s, 2H), 3.82 (s, 3H), 3.70 (s, 2H), 2.84 (t, J=6.5 Hz, 2H), 2.73 (t, J=7.2 Hz, 2H). $^{13}$C NMR (CDCl$_3$): δ 154.4, 149.8, 147.2, 137.4, 133.2, 131.5, 129.8, 128.5, 127.8, 127.3, 120.3, 115.4, 114.0, 112.0, 71.2, 56.0, 53.6, 50.8, 50.6, 35.2. HRMS calc'd for C$_{23}$H$_{26}$NO (M+H)$^+$: 364.1907, found 364.1912.

Compound 2h: 95% $^1$H NMR (CDCl$_3$): δ 7.39-7.29 (m, 5H), 7.18 (t, J=7.8 Hz, 1H), 6.97 (d, J=8.4 Hz, 2H), 6.89 (s, 1H), 6.83 (d, J=8.4 Hz, 1H), 6.82 (d, J=6.4 Hz, 1H), 6.65 (d, J=8.4 Hz, 2H), 4.94 (s, 2H), 3.75 (s, 2H), 2.85 (t, J=6.6 Hz, 2H), 2.73 (t, J=7.0 Hz, 2H). $^{13}$C NMR (CDCl$_3$): δ 159.0, 154.5, 141.4, 137.1, 131.4, 129.8, 129.5, 128.6, 127.9, 127.5, 120.8, 115.5, 114.5, 113.6, 69.9, 53.7, 50.4, 35.1. HRMS calc'd for C$_{22}$H$_{24}$NO$_2$ (M+H)$^+$: 334.1802 found 334.1807.

Compound 2j: 60%; $^1$H NMR (Acetone-d$_6$): δ 7.32 (dd, J=3.0, J=2.5 Hz, 1H), 7.17-7.16 (m, 1H), 7.02 (dd, J=1.0, J=2.5 Hz, 1H), 7.00 (d, J=8.4 Hz, 2H), 6.70 (d, J=8.4 Hz, 2H), 3.75 (s, 2H), 2.75 (t, J=6.9 Hz, 2H), 2.65 (t, J=6.9 Hz, 2H). $^{13}$C NMR (CDCl$_3$): δ 155.6, 142.5, 131.2, 129.5, 127.7, 125.2, 120.9, 115.0, 51.0, 48.4, 35.4. HRMS calc'd for C$_{13}$H$_{16}$NOS (M+H)$^+$: 234.0947, found 234.0952.

Compound 2l: 89%; $^1$H NMR (CDCl$_3$): δ 7.83-7.81 (m, 1H), 7.70-7.67 (m, 1H), 7.35-7.29 (m, 2H), 7.00 (d, J=8.3 Hz, 2H), 6.67 (d, J=8.4 Hz, 2H), 4.03 (s, 2H), 2.94 (t, J=7.0 Hz, 2H), 2.76 (t, J=7.0 Hz, 2H). $^{13}$C NMR (CDCl$_3$): δ 155.6, 140.6, 138.7, 136.1, 131.2, 129.6, 124.2, 123.7, 122.6, 122.6, 122.3, 115.0, 51.3, 47.3, 35.4. HRMS calc'd for C$_{17}$H$_{18}$NOS (M+H)$^+$: 284.1104, found 285.1108.

Example 3: Synthesis of Compounds 3a-h, 3j, and 3l

Reaction II: To a dry flask containing 2.7 mmol of a selected amine 2a-l in 9.6 mL pyridine under argon was added 0.75 mL (5.2 mmol) of trifluoroacetic anhydride. The reaction was stirred at 0° C. for 1 day and quenched with 3 mL of methanol. The solution was concentrated in vacuo, dissolved in ethyl acetate, and washed twice with water and twice with brine. The solution was dried with sodium sulfate, filtered, concentrated in vacuo, and the desired product 3a-h, 3j and 3l was purified by column chromatography (hexanes/ethyl acetate, 1.5:1).

Compound 3c: 82%; $^1$H NMR (CDCl$_3$): δ 6.99 (d, J=11.2 Hz, 2H), 6.95-6.58 (m, 5H), 5.46 (s, 1H), 4.51 (s, 1H), 4.26-4.22 (m, 5H), 3.45-3.41 (m, 2H), 2.78 (t, J=7.1 Hz, 1H), 2.72 (t, J=7.1 Hz, 1H). $^{13}$C NMR (CDCl$_3$): δ 157.5, 157.2, 157.1, 156.8, 154.8, 154.8, 154.6, 143.9, 143.8, 143.6, 143.5, 130.1, 129.9, 129.8, 129.8, 129.2, 128.5, 127.8, 121.3, 120.6, 117.7, 117.7, 117.1, 116.5, 115.8, 115.7, 115.6, 64.4, 51.0, 50.9, 49.1, 48.4, 48.3, 48.3, 41.3, 34.3, 34.1, 31.9. HRMS calc'd for C$_{19}$H$_{18}$F$_3$NNaO$_4$ (M+Na)$^+$: 404.1080, found 404.1085.

Compound 3d: 80%; $^1$H NMR (CDCl$_3$): δ 6.99-6.96 (m, 2H), 6.81-6.72 (m, 5H), 5.94 (d, J=7.0 Hz, 2H), 5.23 (s, 1H), 4.65 (s, 1H), 4.43 (s, 1H), 3.49 (m, 2H), 2.83 (t, J=7.8 Hz, 1H), 2.74 (t, J=7.8 Hz, 1H). $^{13}$C NMR (CDCl$_3$): δ157.6, 157.4, 157.3, 157.0, 155.0, 154.8, 147.6, 147.4, 146.0, 145.8, 129.9, 129.8, 129.7, 129.0, 122.3, 122.3, 122.2, 121.0, 118.1, 118.0, 116.7, 116.1, 115.8, 115.7, 115.6, 115.3, 115.1, 108.7, 108.6, 101.2, 101.1, 48.9, 48.9, 48.7, 46.0, 45.9, 44.2, 34.2, 31.9. HRMS calc'd for C$_{18}$H$_{16}$F$_3$NNaO$_4$ (M+Na)$^+$: 390.0924, found, 390.0927.

Compound 3f: 81%; $^1$H NMR (CDCl$_3$): δ 7.43 (d, J=7.8 Hz, 2H), 7.38-7.34 (m, 2H), 7.32-7.28 (m, 1H), 6.98-6.95 (m, 2H), 6.85 (dd, J=6.6, J=4.0 Hz, 1H), 6.79-6.70 (m, 3H), 6.65-6.61 (m, 1H), 5.15 (d, J=3.8 Hz, 2H), 4.58 (s, 1H), 4.33 (s, 1H), 3.85 (d, J=1.6 Hz, 3H), 3.49-3.43 (m, 2H), 2.80 (t, J=7.4 Hz, 1H), 2.73 (t, J=7.1 Hz, 2H), $^{13}$C NMR (CDCl$_3$): δ 155.1, 154.9, 150.1, 148.2, 148.1, 136.9, 136.8, 129.9, 129.7, 128.9, 128.62, 128.6, 128.4, 128.0, 128.0, 127.5, 127.4, 120.8, 120.2, 115.8, 114.1, 114.0, 111.9, 111.1, 71.1, 56.1, 56.0, 51.4, 51.3, 49.6, 48.4, 34.3, 32.0. HRMS calc'd for C$_{25}$H$_{24}$F$_3$NNaO$_4$ (M+Na)$^+$: 482.1550, found 482.1555.

Compound 3g: 64%; $^1$H NMR (CDCl$_3$): δ 7.42-7.26 (m, 10H), 7.03 (d, J=6.6 Hz, 1H), 6.90 (dd, J=8.4, J=1.8 Hz, 2H), 6.86 (dd, J=8.2, J=3.4 Hz, 1H), 6.79-6.77 (m, 1H), 6.74-6.69 (m, 2H), 5.14 (d, J=2.2 Hz, 2H), 5.12 (s, 2H), 4.49 (s, 1H), 4.21 (s, 1H), 3.36-3.28 (m, 2H), 2.67 (t, J=7.8 Hz, 1H), 2.61 (t, J=7.1 Hz, 1H). $^{13}$C NMR (CDCl$_3$): δ 154.5, 154.3, 149.1, 137.1, 137.0, 136.9, 136.9, 130.4, 129.9, 129.9, 129.8, 129.5, 128.6, 128.5, 128.5, 128.0, 127.9, 127.9, 127.7, 127.4, 127.3, 121.4, 120.8, 115.8, 115.6, 115.5, 115.1, 114.9, 114.5, 71.4, 71.3, 71.2, 49.4, 48.2, 41.2, 34.3, 34.1, 31.9, 29.7. HRMS calc'd for C$_{31}$H$_{28}$F$_3$NNaO$_4$ (M+Na)$^+$: 558.1863, found 558.1863.

Compound 3h: 88%; $^1$H NMR (CDCl$_3$): δ 7.43-7.23 (m, 5H), 6.96-6.91 (m, 3H), 6.83-6.71 (m, 4H), 5.93 (d, J=8.3 Hz, 1H), 5.04 (d, J=4.2 Hz, 1H), 4.61 (s, 1H), 4.35 (s, 1H), 3.48-3.42 (m, 2H), 2.79-2.70 (m, 2H). $^{13}$C NMR (CDCl$_3$): δ 159.3, 159.3, 157.8, 157.5, 157.4, 157.1, 155.0, 154.8, 136.8, 136.7, 136.6, 136.3, 130.2, 130.1, 129.9, 129.8, 129.0, 128.7, 128.7, 128.2, 128.1, 127.5, 120.6, 120.0, 115.8, 115.7, 114.7 114.6, 114.2, 70.2, 70.1, 51.52, 51.49, 49.8, 48.7, 34.3, 31.9. HRMS calc'd for C$_{24}$H$_{22}$F$_3$NNaO$_3$ (M+Na)$^+$: 452.1444, found 452.1448.

Compound 3j: 77%; $^1$H NMR (CDCl$_3$): δ 7.33-7.28 (m, 1H), 7.15-7.07 (m, 1H), 6.98-6.9 (m, 2H), 6.78-6.74 (m, 2H), 4.60 (s, 1H), 4.37 (s, 1H), 3.51-3.45 (m, 2H), 2.79 (t, J=7.8 Hz, 1H), 2.70 (t, J=7.2 Hz, 1H). $^{13}$C NMR (CDCl$_3$): δ 157.4, 157.1, 156.9, 156.6, 154.8, 154.6, 135.9, 135.7, 130.0, 129.9, 129.8, 129.2, 127.5, 127.2, 126.9, 126.7, 123.8, 123.6, 115.7, 115.6, 48.64, 48.59, 47.1, 47.0, 45.2, 34.4, 32.0. HRMS calc'd for $C_{15}H_{14}F_3NNaO_2S$ (M+Na)$^+$: 352.0590, found 352.0595.

Compound 3l: 95%; $^1$H NMR (CDCl$_3$): δ 7.88-7.84 (m, 1H), 7.72-7.70 (m, 1H), 7.41-7.36 (m, 2H), 7.30 (s, 1H), 6.95-6.92 (m, 2H), 6.77-6.73 (m, 2H), 5.29 (broad s, 1H), 4.89 (s, 1H), 4.60 (s, 1H), 3.52 (t, J=7.1 Hz, 1H), 3.46 (t, J=7.1 Hz, 1H), 2.80-2.73 (m, 2H). $^{13}$C NMR (CDCl$_3$): δ 157.6, 157.2, 154.8, 154.7, 140.7, 140.5, 137.6, 137.3, 130.0, 129.9, 129.8, 129.6, 129.1, 126.0, 125.03, 124.97, 124.74, 124.70, 124.6, 123.2, 123.1, 121.6, 120.9, 118.1, 115.8, 115.6, 115.3, 49.0, 48.17, 48.15, 46.3, 46.2, 43.6, 34.5, 32.2. HRMS calc'd for $C_{19}H_{16}F_3NNaO_2S$ (M+Na)$^+$: 402.0746, found 402.0752.

Example 4: Synthesis of Compounds 4a-l

Reaction III: To a dry flask containing 1.2 mmol of a selected coupling precursor 3a-l in 6 mL of 2,2,2-trifluoroethanol under argon was added 0.5956 g (1.4 mmol) phenyliodine bis(trifluoroacetate) dissolved in 6 mL of 2,2, 2-trifluoroethanol. The reaction was stirred at −40° C. for 30 min, and the solution was concentrated in vacuo. Purification by column chromatography (hexanes/ethyl acetate, 2:1) yielded pure spirodienone 4a-l.

Compound 4c: 36%; $^1$H NMR (CDCl$_3$): δ 7.00 (d, J=10.1 Hz, 1H), 6.88 (d, J=10.1 Hz, 1H), 6.81 (s, 1H), 6.65 (s, 1H), 6.55 (s, 1H), 6.24 (d, J=9.9 Hz, 1H), 6.22 (d, J=9.9 Hz, 1H), 4.69 (d, J=6.6 Hz, 2H), 4.19-4.14 (m, 4H), 3.92-3.86 (m, 2H), 2.31 (tt, J=17.5 Hz, 6.2 Hz, 2H). $^{13}$C NMR (CDCl$_3$): δ 185.3, 185.2, 156.9, 156.5, 156.2, 155.9, 152.8, 152.3, 143.4, 143.3, 142.8, 142.8, 129.0, 128.9, 128.5, 128.4, 127.2, 127.0, 120.2, 118.9, 118.6, 77.4, 77.1, 76.8, 64.4, 64.4, 64.3, 48.7, 48.7, 48.5, 48.2, 47.9, 45.6, 45.5, 44.3, 36.1, 33.9. HRMS calc'd for $C_{19}H_{16}F_3NNaO_4$ (M+Na)$^+$: 402.0924, found 402.0926.

Compound 4d: 26%; $^1$H NMR (CDCl$_3$): δ 6.99 (d, J=10.3 Hz, 1H), 6.86 (d, J=10.3 Hz, 1H), 6.65-6.54 (m, 2H), 6.26-6.22 (m, 2H), 5.98 (d, J=14.1 Hz, 2H), 4.85 (d, J=15.4 Hz, 2H), 3.95-3.91 (m, 2H), 2.37-2.31 (m, 2H). $^{13}$C NMR (CDCl$_3$): δ 185.3, 185.1, 152.5, 152.2, 146.9, 146.7, 146.5, 146.0, 129.9, 129.84, 127.1, 126.9, 123.5, 123.1, 117.8, 117.3, 108.3, 108.1, 101.7, 101.6, 48.4, 48.0, 44.6, 41.0, 36.2, 34.2. HRMS calc'd for $C_{18}H_{14}F_3NNaO_4$ (M+Na)$^+$: 388.0767, found 388.0773.

Compound 4f: 41%; $^1$H NMR (CDCl$_3$): δ 7.32-7.24 (m, 5H), 6.85 (d, J=10.0 Hz, 1H), 6.76 (d, J=13.4 Hz, 1H), 6.70 (d, J=35.9 Hz, 1H), 6.47 (d, J=2.6 Hz, 1H), 6.17 (dd, J=10.1, J=3.1 Hz, 2H), 5.00 (s, 2H), 4.73 (d, J=14.6 Hz, 2H), 3.88 (s, 3H), 3.86 (s, 2H), 2.33-2.27 (m, 2H). $^{13}$C NMR (CDCl$_3$): δ 185.1, 185.0, 156.8, 156.5, 156.4, 156.0, 152.7, 152.3, 148.8, 148.8, 147.6, 147.5, 136.6, 136.5, 128.7, 128.6, 128.3, 128.1, 128.0, 128.0, 127.8, 127.6, 127.4, 127.3, 127.3, 127.2, 127.1, 116.1, 114.5, 113.5, 71.3, 71.2, 56.2, 56.1, 48.3, 48.2, 48.0, 44.2, 35.5, 33.6. HRMS calc'd for $C_{25}H_{22}F_3NNaO_4$ (M+Na)$^+$: 480.1393, found 480.1398.

Compound 4g: 20% $^1$H NMR (CDCl$_3$): δ 7.43-7.24 (m, 10H), 6.87 (d, J=9.4 Hz, 1H), 6.76 (d, J=10.0 Hz, 1H), 6.63 (s, 1H), 6.50 (d, J=1.6 Hz, 1H), 6.19 (dd, J=9.9 Hz, J=6.7 2H), 5.19 (s, 2H), 5.01 (d, J=2.4 Hz, 2H), 4.67 (d, J=14.2 Hz, 2H), 3.89-3.84 (m, 2H), 2.32-2.26 (m, 2H). $^{13}$C NMR (CDCl$_3$): δ 185.2, 185.1, 152.7, 152.3, 148.3, 148.2, 148.1, 147.9, 136.7, 136.7, 136.6, 136.6, 128.6, 128.6, 128.5, 128.4, 128.3, 128.2, 128.1, 128.0, 128.0, 127.4, 127.3, 127.3, 127.1, 117.1, 117.0, 116.8, 116.6, 71.4, 71.4, 71.3, 71.2, 48.3, 48.2, 48.0, 45.3, 44.2, 35.5, 33.6, 29.7. HRMS calc'd for $C_{31}H_{26}F_3NNaO_4$ (M+Na)$^+$: 556.1712, found 556.1715.

Compound 4h: 21%; $^1$H NMR (CDCl$_3$): δ 7.39-7.30 (m, 5H), 7.02-6.95 (m, 3H), 6.89 (d, J=10.2 Hz, 1H), 6.82-6.77 (m, 1H), 6.29-6.25 (m, 2H), 5.02 (s, 2H), 4.78 (d, J=8.0 Hz, 2H), 3.96-3.90 (m, 2H), 2.38-2.31 (m, 2H). $^{13}$C NMR (CDCl$_3$): δ 185.3, 185.2, 128.2, 128.1, 152.8, 152.4, 136.7, 136.7, 136.5, 136.4, 131.7, 131.2, 128.68, 128.65, 128.2, 128.1, 127.5, 127.4, 127.3, 127.1, 117.8, 117.0, 114.8, 114.7, 70.2, 70.1, 49.34, 49.31, 49.1, 48.2, 47.9, 45.6, 45.5, 44.5, 36.1, 34.0. HRMS calc'd for $C_{24}H_{20}F_3NNaO_3$ (M+Na)$^+$: 450.1287, found 450.1292.

Compound 4i: 11%; $^1$H NMR (CDCl$_3$): δ 7.31-7.29 (m, 3H), 7.24-7.15 (m, 3H), 6.95-6.77 (m, 4H), 6.08 (d, J=10.0 Hz, 2H), 4.86 (s, 2H), 4.84 (s, 2H), 3.88-3.81 (m, 2H), 2.34-2.31 (m, 2H). $^{13}$C NMR (CDCl$_3$): δ 185.04, 184.99, 158.4, 158.4, 156.8, 156.5, 156.1, 153.5, 153.3, 137.4, 137.3, 135.4, 135.3, 129.1, 128.62, 128.60, 128.32, 128.28, 127.9, 127.43, 127.41, 125.3, 125.0, 123.8, 122.9, 112.6, 112.5, 70.9, 48.8, 48.8, 47.8, 47.4, 47.1, 45.2, 45.1, 44.2, 38.4, 37.0.

Compound 4l: 41%; $^1$H NMR (CDCl$_3$): δ 7.84 (d, J=8.1, 1H), 7.71 (t, J=7.8 Hz, 1H), 7.63 (d, J=8.1 Hz, 1H), 7.43-7.31 (m, 2H), 7.13-7.11 (m, 1H), 7.02-6.99 (m, 1H), 6.36-6.32 (m, 2H), 5.05 (s, 1H), 4.98 (s, 1H), 4.11-4.08 (m, 2H), 2.45-2.39 (m, 2H). $^{13}$C NMR (CDCl$_3$): δ 184.7, 156.6, 150.0, 149.5, 140.2, 139.5, 138.8, 138.3, 137.8, 130.3, 129.8, 128.6, 128.4, 125.3, 125.0, 124.8, 122.6, 122.4, 121.4, 121.0, 46.0, 45.7, 45.6, 45.0, 42.8, 41.9, 37.5, 35.7. HRMS calc'd for $C_{23}H_{26}F_3NNaO_2S$ (M+Na)$^+$: 400.0590, found 400.0593.

Example 5: Synthesis of Compounds 5a-l

Reaction IV: To a flask containing 0.15 mmol of a selected spirodienone in 0.78 mL of methanol was added 0.8 mL of 10% aqueous potassium hydroxide at room temperature. The reaction was stirred for 30 min, and the solution was extracted several times with chloroform. The organic layers were collected, filtered, and concentrated in vacuo. Purification by column chromatography (chloroform/methanol, 14:1) yielded the desired 5,10b-ethanophenanthridine.

Compound 5c: 66%; $^1$H NMR (CDCl$_3$): δ 7.60 (d, J=10.3 Hz, 1H), 6.87 (s, 1H), 6.53 (s, 1H), 6.05 (d. J=10.3 Hz, 1H), 4.35 (d, J=16.9 Hz, 1H), 4.23-4.19 (m, 4H), 3.77 (d, J=17.0 Hz, 1H), 3.60 (dd, J=13.0 Hz, 5.7 Hz, 1H), 3.54-3.47 (m, 1H), 3.02-2.95 (m, 1H), 2.65 (dd, J=16.8 Hz, 5.7 Hz, 1H), 2.44 (dd, J=16.7 Hz, 13.0 Hz, 1H), 2.37-2.31 (m, 1H), 2.18-2.10 (m, 1H). 13C NMR (CDCl3): δ 198.2, 149.6, 142.3, 142.1, 136.0, 128.7, 126.1, 115.7, 110.7, 68.9, 64.5, 64.4, 61.3, 54.0, 44.6, 44.3, 40.1. HRMS calc'd for $C_{17}H_{18}NO_3$ (M+H)$^+$: 284.1281, found 284.1287.

Compound 5d: 53%; $^1$H NMR (CDCl$_3$): δ 7.65 (d, J=10.3 Hz, 1H), 6.84 (d, J=10.3 Hz, 1H), 6.67 (d, J=10.3 Hz, 1H), 6.05 (d, J=10.3 Hz, 1H), 5.92 (d, J=8.8 Hz, 1H), 4.30 (d, J=17.4 Hz, 1H), 3.85 (d, J=17.4 Hz, 1H), 3.62-3.51 (m, 2H), 3.04-2.97 (m, 1H), 2.70 (dd, J=16.8 Hz, 5.6 Hz, 1H), 2.47 (dd, J=16.8 Hz, 13.0 Hz, 1H), 2.37-2.31 (m, 1H), 2.22-2.14 (m, 1H). $^{13}$C NMR (CDCl$_3$): δ 198.0, 149.5, 145.8, 145.1, 137.3, 128.5, 114.8, 114.3, 106.4, 101.4, 68.8, 56.9, 54.3, 44.8, 44.7, 40.1. HRMS calc'd for $C_{16}H_{16}NO_3$ (M+H)$^+$: 270.1125, found 270.1130.

Compound 5l: Characterization: 74%; $^1$H NMR (CDCl$_3$): δ 7.82 (d, J=7.4 Hz, 1H), 7.46 (d, J=7.4 Hz, 1H), 7.38-7.30 (m. 2H), 6.11 (d, J=10.0 Hz, 1H), 4.44 (d, J=16.6 Hz, 1H), 3.96 (d, J=16.6 Hz, 1H), 3.80 (dd, J=12.9 Hz, 5.8 Hz, 1H), 3.67-3.60 (m, 1H), 3.09-3.01 (m, 1H), 2.78 (dd, J=17.0 Hz, 5.6 Hz, 1H), 2.66-2.59 (m, 2H), 2.52 (dd, J=16.9 Hz, 13.0 Hz, 1H), 2.25-2.18 (m, 1H). $^{13}$C NMR (CDCl$_3$): δ 197.7, 149.7, 138.3, 129.6, 126.1, 124.6, 124.2, 122.9, 120.8, 70.7, 58.1, 54.6, 45.9, 45.0, 40.3, 29.3. HRMS calc'd for C$_{17}$H$_{16}$NOS (M+H)$^+$: 282.0947, found 282.0952.

Example 6: Cell Culture

Human cancer cell lines were obtained from the American Type Culture Collection (ATCC, Manassas, Va., USA), the European Collection of Cell Culture (ECACC, Salisbury, UK), and the Deutsche Sammlung von Mikroorganismen und Zellkulturen (DSMZ, Braunschweig, Germany). Human cervical adenocarcinoma HeLa cells were cultured in DMEM supplemented with 10% fetal bovine serum (FBS). Human mammary carcinoma MCF-7 cells were cultured in RPMI supplemented with 10% FBS. The U87 cells (ATCC HTB-14) were cultured in DMEM culture medium, while the A549 cells (DSMZ ACC107) were cultured in RPMI culture medium supplemented with 10% heat-inactivated FBS. The GBM Hs683 (ATCC HTB-138) and the T98G (ATCC CRL-1690) cell lines were cultivated in DMEM supplemented with 10% FBS. The GBM U251 cells (ECACC code 09063001) were cultured in 10% MEM. The human uterine sarcoma MES-SA and MES-SA/Dx5 cells were cultured in RPMI-1640 medium supplemented with 10% FBS with MES SA/Dx5 maintained in the presence of 500 nM Doxorubicin (Sigma™). The U373 glioblastoma cells (ECACC 08061901) were cultured in RPMI culture medium supplemented with 10% heat-inactivated FBS.

Cell culture media were supplemented with 4 mM glutamine (Lonza code BE17-605E), 100 µg/mL gentamicin (Lonza code 17-5182), and penicillin-streptomycin (200 units/ml and 200 µg/ml) (Lonza code 17-602E). Primary GBM-derived neurosphere cultures from a patient undergoing surgical debulking were established using previously described methods. Briefly, resected tumor tissue was minced with a sterile scalpel and dissociated in 3 mL of neurobasal (NB) media containing 100 U/mL of collagenase (Life Technologies™) for 30 minutes at 37° C. Dissociated tissue was then vortexed and filtered using a sterile 70 um nylon Falcon™ cell strainer (Corning™).

The filtered fraction was spun via centrifuge at 200×g for 5 minutes, and the resultant pellet was transferred to a Corning™ ultra-low attachment plate containing neurobasal medium (Invitrogen™) supplemented with the following: B27 supplement (1X; Invitrogen™), Glutamax (10 ul/ml; Invitrogen™), fibroblast growth factor-2 (20 ug/ml; Peprotech™), epidermal growth factor (20 ug/ml; Peprotech™), heparin (32 ku/ml; Sigma Aldrich™, St. Louis, Mo.) and penicillin-streptomycin (1X, Invitrogen™). GBM 090909 and GBM 031810 cell lines were maintained in NB media containing supplements and media were renewed twice weekly.

NSCLC cell lines H1993 and H2073 were obtained from the Hamon Center for Therapeutic Oncology Research at UT Southwestern Medical Center and cultured in RPMI-1640 medium (Mediatech, VA, USA) supplemented with 5% heat-inactivated FBS (Mediatech™), 100 units/mL penicillin and 0.1 mg/mL streptomycin (Sigma™). All cell lines were cultured in T25 flasks, maintained, and grown at 37° C., 95% humidity, 5% CO$_2$.

Example 7: Antiproliferative Activities of Spirodienones 4a-m

Spirodienones 4a-m were subjected to in vitro growth inhibition 3-(4,5-dimethylthiazol-2-yl)-2,5-diphenyltetrazolium bromide (MTT) assays against two cell lines, human HeLa cervical and MCF-7 breast adenocarcinomas. TABLE 2 demonstrates that Spirodienones 4a-4m produced a range of activities, as observed in the potency of 4l, inactivity of 4m, and moderate activity of 4a.

All compounds were dissolved in DMSO at a concentration of either 100 mM or 50 mM prior to cell treatment. The cells were trypsinized and seeded at various cell concentrations depending on the cell type. The cells were grown for 24 h to 72 h, treated with compounds at concentrations ranging from 0.001 to 100 µM, and incubated for 48, 72, or 96 h in 100 or 200 µL media depending on the cell line used. Cells treated with 0.1% DMSO were used as a negative control, and cells treated with 1 µM phenyl arsine oxide (PAO) were used as a positive control.

TABLE 2

| | cell viability$^a$ GI$_{50}$, µM | |
|---|---|---|
| compound | HeLa | MCF-7 |
| 4a | 24 ± 2 | 30 ± 2 |
| 4b | 83 ± 5 | >100 |
| 4c | 21 ± 1 | 34 ± 12 |
| 4d | >100 | >100 |
| 4e | 38 ± 2 | 48 ± 3 |
| 4f | 34 ± 4 | 34 ± 2 |
| 4g | 17 ± 1 | 25 ± 2 |
| 4h | 16 ± 0 | 40 ± 1 |
| 4i | 11 ± 2 | 14 ± 2 |
| 4j | NI$^b$ | NI |
| 4k | NI | NI |
| 4l | 10 ± 0 | 7 ± 1 |
| 4m | >100 | >100 |

$^a$Concentration required to reduce the viability of cells by 50% after a 48 h treatment with the indicated compounds relative to a DMSO control ± SD from two independent experiments, each performed in 4 replicates, as determined by the MTT assay.
$^b$NI = not isolated in pure form Example 8: Antiproliferative Activities of Spirodienone 4l Against Cancer Cells Displaying Drug Resistance Compound 4l was evaluated for in vitro growth inhibition against a panel of cancer cell lines, including U373, U251, U87, T98G, human GBM, and A549 NSCLC. All of the cells exhibit various degrees and mechanisms of apoptosis resistance. Compound 4l was also evaluated for in vitro growth inhibition against the apoptosis-sensitive tumor model Hs683 anaplastic oligodendroglioma as a reference. TABLE 3 demonstrates the obtained GI$_{50}$ values associated with spirodienone 4l, bulbispermine, TMZ, and paclitaxel. The data reveal that the compound retains single-digit micromolar antiproliferative GI$_{50}$ values, and is more potent than bulbispermine, which displayed double-digit micromolar potencies.

Compound 4l was also evaluated against the MDR uterine sarcoma cell line (MES-SA/Dx5 to evaluate whether the compounds of the invention were substrates for the MDR cancer efflux systems. The MES-SA/Dx5 cell line was established from the parent uterine sarcoma MES-SA, grown in the presence of increasing concentrations of doxorubicin and is known to be resistant to a number of P-gp substrates.

The selection of doxorubicin-resistant cells (MES-SA/Dx5 cell line) was performed by splitting the cells and allowing the cells to adhere overnight. The next day, the cells were initially exposed to a DOX concentration of 100 nM, which represented the $GI_{50}$ concentration. The cells were maintained at this DOX concentration until their growth rate reached that of the untreated cells. The DOX concentration was then increased in two-fold increments following the same growth criteria at each concentration to a final DOX concentration of 500 nM. Each new DOX concentration required approximately 2 passages to reach the growth rate of the untreated cells.

Both paclitaxel and vinblastine (not shown) displayed more than a 1000-fold drop in potency when tested for antiproliferative activity against the MDR cell line as compared to the parent cell line. The results in TABLE 3 demonstrate that 4l only had a small variation in activity, indicating potential to overcome clinical multi-drug resistance.

96-well plates. The cells were grown for 24 h and treated with paclitaxel and 4l, alone or in combination. After 96 h, viability of cells was assessed using the CellTiter-Glo® Luminescent Cell Viability Assay (Promega™), according to the manufacturer's instructions. Predicted additivity was calculated based on Bliss Independence, as defined by $E_{xy}=E_x+E_y-E_xE_y$, where $E_{xy}$ is the additive effect of drugs x and y as predicted by the individual effects $E_x$ and $E_y$.

Figure 2:
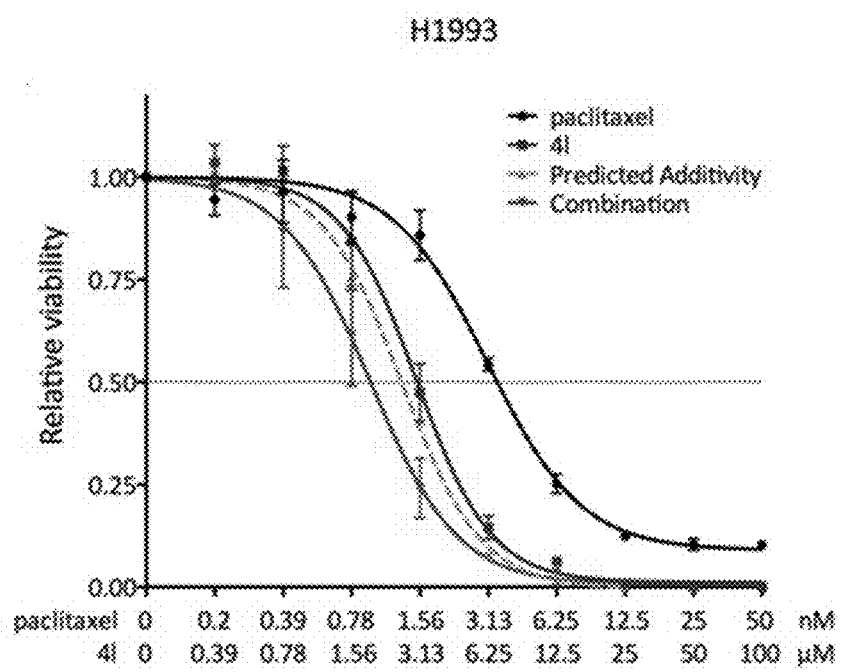
FIG. 2 illustrates results of the combination treatment of paclitaxel with compound 4l against H1993 cells.
Figure 3:
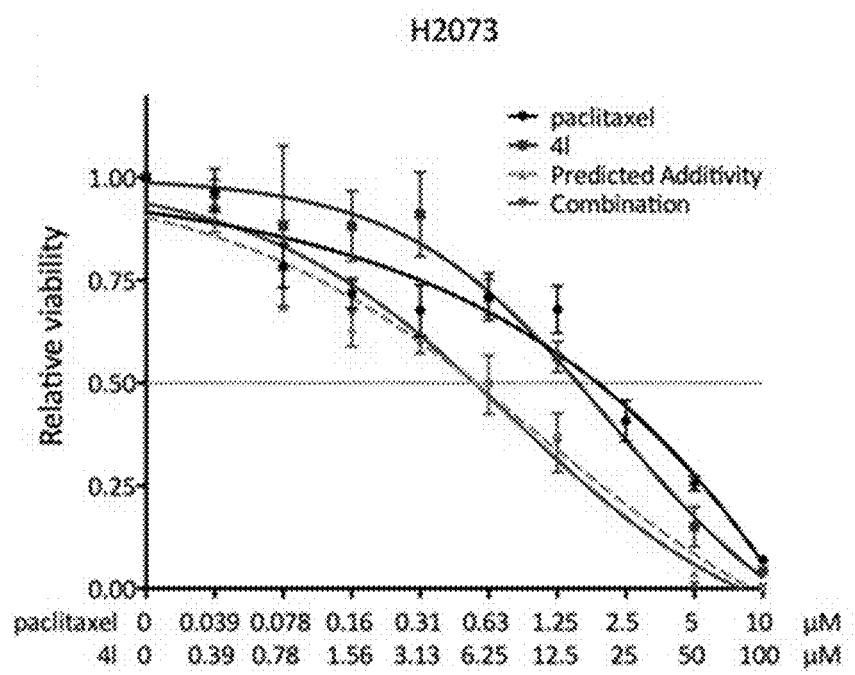
FIG. 3 illustrates results of the combination treatment of paclitaxel with compound 4l against H2073 cells.

FIG. 2 shows the combination treatment of paclitaxel with compound 4l against H1993 cells. FIG. 3 shows the combination treatment of paclitaxel with compound 4l against H2073 cells. FIG. 2 and FIG. 3 illustrate the synergism against H1993 cells.

TABLE 3

| | $GI_{50}$ in vitro values (μM)[a] | | | | | | | | | | | |
|---|---|---|---|---|---|---|---|---|---|---|---|---|
| | glioma | | | | | | | lung cancer | | | uterine sarcoma | |
| | | | | | | GBM | GBM | | | | MES- | MES- |
| compound | Hs683 | U373 | U251 | U87 | T98G | 090909 | 031810 | A549 | H1993 | H2073 | SA | SA/Dx5 |
| 4l | 5 | 7 | 4 | 6 | 15 | 7 | 8 | —[b] | 12 | 50 | 5 | 5 |
| bulbispermine | 27 | 53 | 41 | 38 | 99 | — | — | — | — | — | — | — |
| TMZ | — | — | — | — | — | 50 | >1000 | — | — | — | — | — |
| paclitaxel | — | — | — | — | — | — | — | — | 0.004 | 2.4 | 0.007 | 10 |

[a]Average concentration required to reduce the viability of cells by 50% after a 48-96 h treatment with the indicated compounds in varied numbers of replicates, as determined by the MTT assay.
[b]— = not tested

Example 9: Activity of Spirodienone 4l Against Cell Populations Resistant to Proapoptotic Agents Determined with the MTT Assay Cells resistant to various pro-apoptotic stimuli often contain a sensitive population that quickly response to pro-apoptotic agents. However, a significant portion of the cells in a culture resist the effects of pro-apoptotic agents even at concentrations 100- or 1000-fold their $GI_{50}$ values. The absence of such resistant populations in 5 GBM cell lines treated with spirodienone 4l was observed. FIG. 1 shows the growth curves of five GBM cell cultures treated with 4l (one experiment performed in six replicates).

Example 10: Evaluation of Synergism of Compound 4l with Paclitaxel

Spirodienone 4l was evaluated against patient-derived NSCLC cell line H1993 and its drug-resistant variant, H2073. The patient-derived NSCLC cell line H1993 was obtained from a regrown tumor at a primary site after a patient relapsed several months later. The drug resistance of H2073 cells was exemplified by the loss of responsiveness toward paclitaxel by several orders of magnitude relative to H1993 cells (TABLE 3). TABLE 3 demonstrates that although the potency of 4l decreased against the H2073 cells, the drop was significantly less pronounced than that observed with paclitaxel. Compound 4l was also found to synergize with paclitaxel in its antiproliferative action against the H1993 cell line.

Paclitaxel (Teva™) was dissolved in polyethoxylated castor oil. Compound 4l was dissolved in DMSO. The compound was diluted to different concentrations in medium. Appropriate numbers of cells ($4 \times 10^3$ cells per well for H1993, $7 \times 10^3$ cells per well for H2073) were seeded into

Example 11: Growth Inhibitory Activities of Compounds 5a-l Against Human Cancer Cell Lines To determine the activities of the compounds of the invention toward cancer cells, cell lines treated with different compounds were subjected to an in vitro MTT growth assay using human cervical cancer (HeLa) and human adenocarcinoma (MCF-7) cell lines. The MTT growth assay is a colorimetric assay that measures the metabolic activity of cells via reduction of 3-(4,5-dimethylthiazol-2-yl)-2,5-diphenyltetrazolium bromide (MTT). The reduction of MTT occurs in metabolically-active cells and is characterized by a purple color, which can be quantified via spectrophotometry. A higher absorbance reading indicates a metabolically-active cell, while a low absorbance reading indicates low metabolic activity due to, for example, inhibition of cellular proliferation or cell death.

The concentrations for 50% of maximal inhibition of cell proliferation ($GI_{50}$) values were determined after a 48-hour treatment with the indicated compounds relative to a dimethyl sulfoxide (DMSO) control. The values in TABLE 4 are the mean and standard deviation calculated from two independent experiments, which were performed in 4 replicates.

The results of the experiments are displayed in TABLE 4. For compounds containing a C3-carbonyl moiety, such as compounds 5a-i, the $GI_{50}$ values ranged from low to greater than 100 μM. High potency of the compounds appeared to be associated with compounds containing large hydrophobic substituents in the aromatic ring portion of the molecules as seen in compounds 5e-i. Compounds 5l and 5g, which incorporate two benzyl substituents or a benzothiophene-based bicyclic ring system, respectively, had low $GI_{50}$ values. Haemanthamine, a highly potent crinine analogue, was used as a control compound.

TABLE 4

| Compound | HeLa Cell Viability GI$_{50}$ (μM) | MCF-7 Cell Viability GI$_{50}$ (μM) |
|---|---|---|
| 5a | 25.4 ± 3 | 23.9 ± 0.7 |
| 5b | 63.5 ± 2.7 | >100 |
| 5c | 12.7 ± 2.3 | 18.6 ± 0.8 |
| 5d | 60.5 ± 4.7 | 72.5 ± 2.5 |
| 5e | 11.8 ± 0.5 | 14.5 ± 1 |
| 5f | 16.7 ± 1.8 | 16.8 ± 0.2 |
| 5g | 3.3 ± 0.6 | 3.5 ± 0.3 |

TABLE 4-continued

| Compound | HeLa Cell Viability GI$_{50}$ (μM) | MCF-7 Cell Viability GI$_{50}$ (μM) |
|---|---|---|
| 5h | 7.9 ± 0.3 | 14.4 ± 1 |
| 5i | 7.37 ± 0.9 | 11 ± 0.7 |
| 5j | 8.4 ± 1.1 | 11.6 ± 0.4 |
| 5k | 25.4 ± 5.2 | 43.6 ± 2.1 |
| 5l | 6.2 ± 1.13 | 4.7 ± 0.1 |
| Haemanthamine | 1.8 ± 0.3 | 2.1 ± 0.2 |

Example 12: Growth Inhibitory Activities of Compounds 5l and 5g Against Human Cancer Cell Lines Displaying Drug-Resistance Due to their high potencies, compounds 5l and 5g were used to determine the effects of the compounds on drug-resistant tumor cells. A panel of drug-resistant cell lines was chosen for analysis as shown in TABLE 5. Drug-resistant cell lines (i.e., glioma: Hs683, U373, U251, U87, T98G; lung cancer: A549, H2073; uterine carcinoma: MES-SA/Dx5) were complemented with drug-sensitive cell lines, H1993 lung cancer and MES-SA uterine cancer, which were used as controls. Bulbispermine and paclitaxel were also used as controls. The GI$_{50}$ values were calculated after 48-96 hours of treatment with the indicated compounds in replicate using the MTT growth assay.

The results in TABLE 5 indicated that compounds 5l and 5g displayed higher potency than did bulbispermine against the drug-resistant cell lines. The ability of the compounds 5l and 5g to overcome drug-resistance is demonstrated by similar potencies in drug-resistant and -sensitive cell lines. In contrast, the widely used chemotherapeutic agent paclitaxel lost potency when tested against H1993 and its drug resistant variant H2073 (apoptosis resistance), and MES-SA and its drug-resistant variant MES-SA/Dx5 (multidrug resistance, MDR).

Compound 5l was further tested to determine the effect of compounds of the invention on drug-resistant tumor cells. A patient-derived non-small cell lung cancer (NSCLC) line, H1993, and the drug-resistant variant of H1993, H2073, were used for testing. The H1993 cell line was obtained from a lymph node metastasis isolated from the patient prior to chemotherapy. The H2073 cell line was derived from a regrown tumor at the primary site after the patient had relapsed several months after administration of the chemotherapy regimen. The data in TABLE 5 also indicate that while paclitaxel lost effectiveness toward H2073 cells by almost three orders of magnitude, the decrease in potency of compound 5l toward the H2073 cells was less drastic.

TABLE 5

| | GI$_{50}$ (μM) | | | | | | | | |
|---|---|---|---|---|---|---|---|---|---|
| | Glioma | | | | | Lung Cancer | | | Sarcoma |
| Compound | Hs683 | U373 | U251 | U87 | T98G | A549 | H1993 | H2073 | MES-SA | MES-SA/Dx5 |
| 2 | 6 | 7 | 5 | 5 | 7 | 4 | 3 | 11 | 2 | 7 |
| 12 | 3 | 2 | 1 | 2 | 7 | 9 | — | — | 5 | 7 |
| BS$^a$ | 27 | 53 | 41 | 38 | 99 | — | — | — | — | — |
| PT$^b$ | — | — | — | — | — | — | 0.004 | 2.4 | 0.007 | 10 |

$^a$bulbispermine;
$^b$paclitaxel

Figure 6:
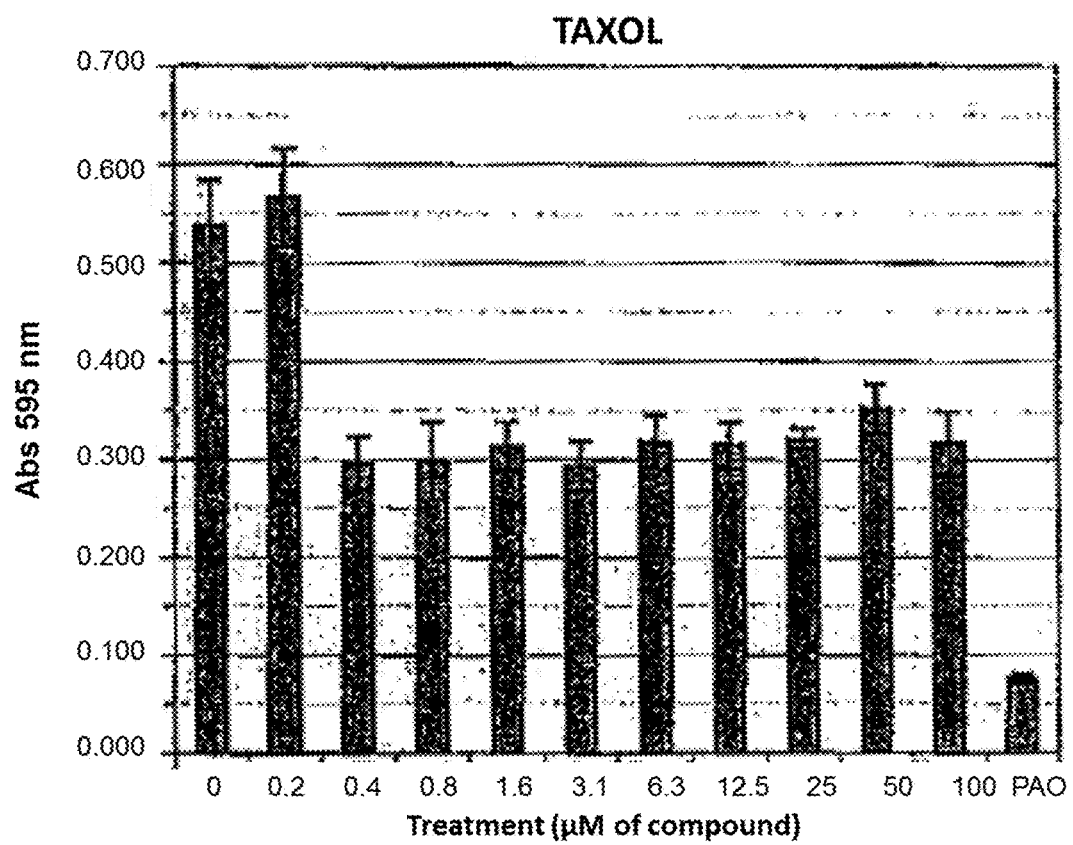
FIG. 6 depicts the effect of Taxol™ on drug-resistant A549 non-small cell lung cancer cells.
Figure 7:
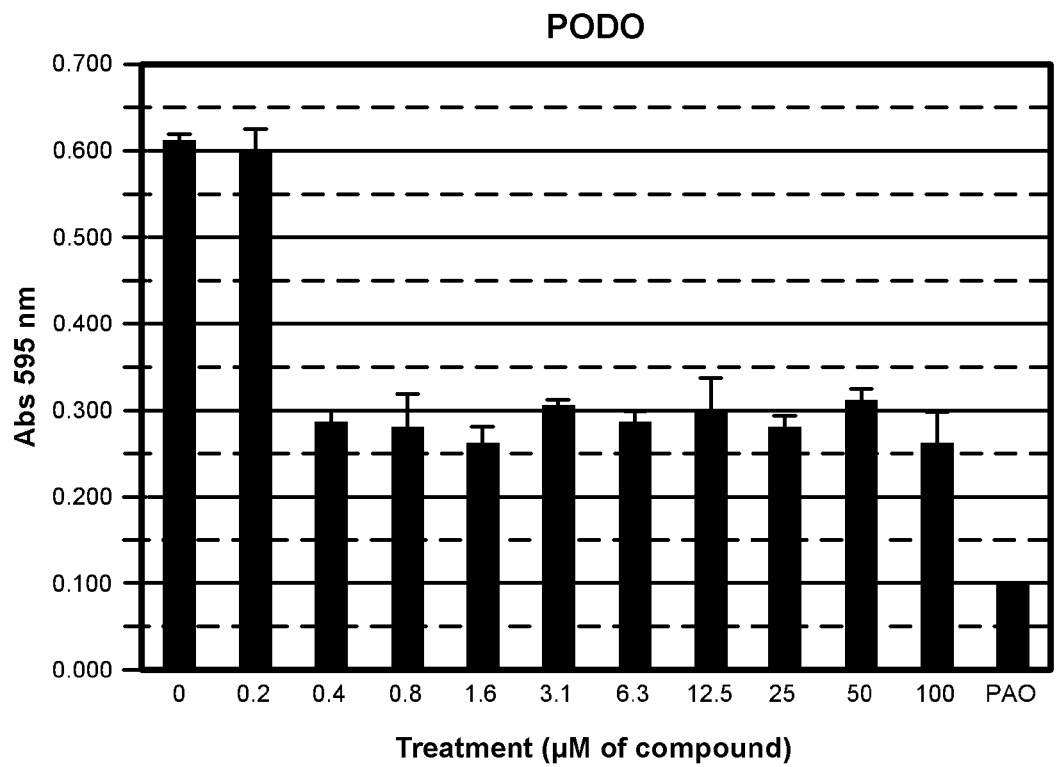
FIG. 7 depicts the effect of podophyllotoxin on drug-resistant A549 non-small cell lung cancer cells.

Compounds 5l and 5g were further tested using the A549 lung cancer cell line to determine a dose-response effect on apoptosis-resistant cells. (FIGS. 4-7). The cells were treated with compound 5l (FIG. 4), compound 5g (FIG. 5), paclitaxel (Taxol™; FIG. 6), podophyllotoxin (PODO; FIG. 7), and phenylarsine oxide (PAO). The MTT assay was performed in four replicates after 48 hours of treatment with the indicated compounds relative to a DMSO control. The results display the mean and standard deviation of two independent experiments. The y-axis of the graphs of FIGS. 4-7 displays the absorbance of the samples at 595 nm, and the x-axis shows the concentration of the indicated compounds (μM).

Figure 4:
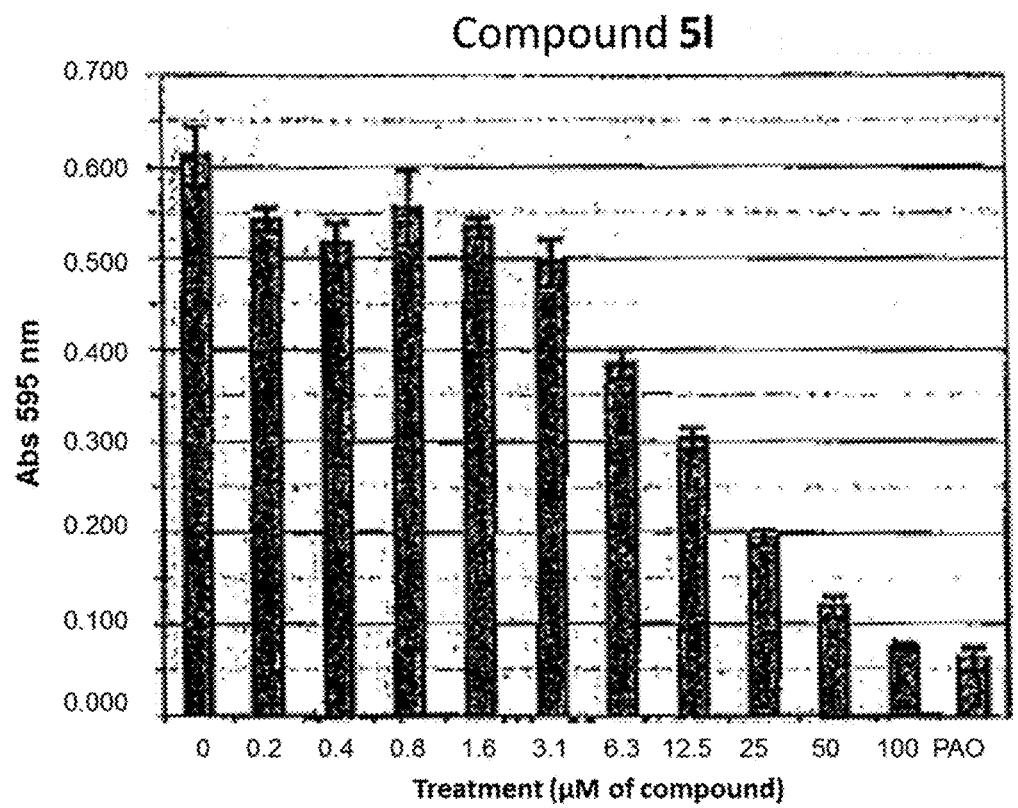
FIG. 4 depicts the effect of Compound 5l on drug-resistant A549 non-small cell lung cancer cells.
Figure 5:
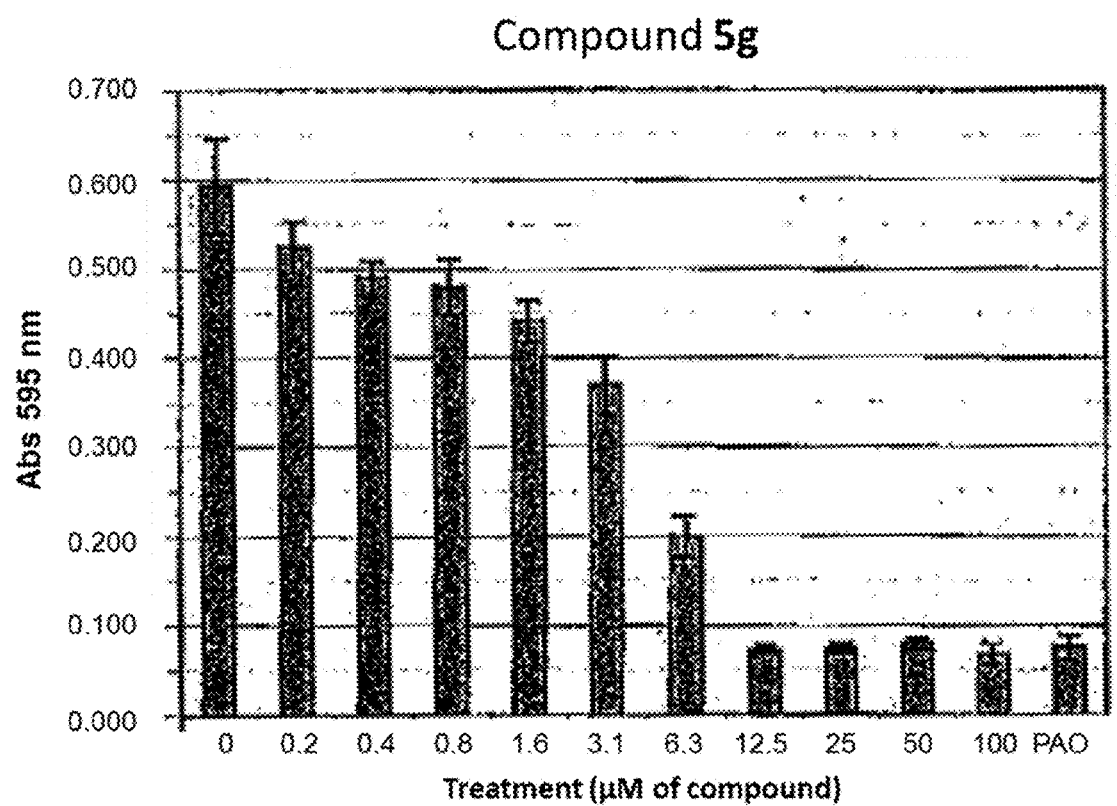
FIG. 5 depicts the effect of Compound 5g on drug-resistant A549 non-small cell lung cancer cells.

FIGS. 4 and 5 show that increasing concentrations of compounds 5l and 5g inhibited proliferation of the cells in a dose-dependent manner. At the highest concentrations of the compounds, the anti-proliferative activity reached levels of the non-specific cytotoxic agent, PAO. In contrast, paclitaxel (FIG. 6) and PODO (FIG. 7) did not display such potent anti-proliferative activity even at concentrations as high as 100 μM.

Figure 8:
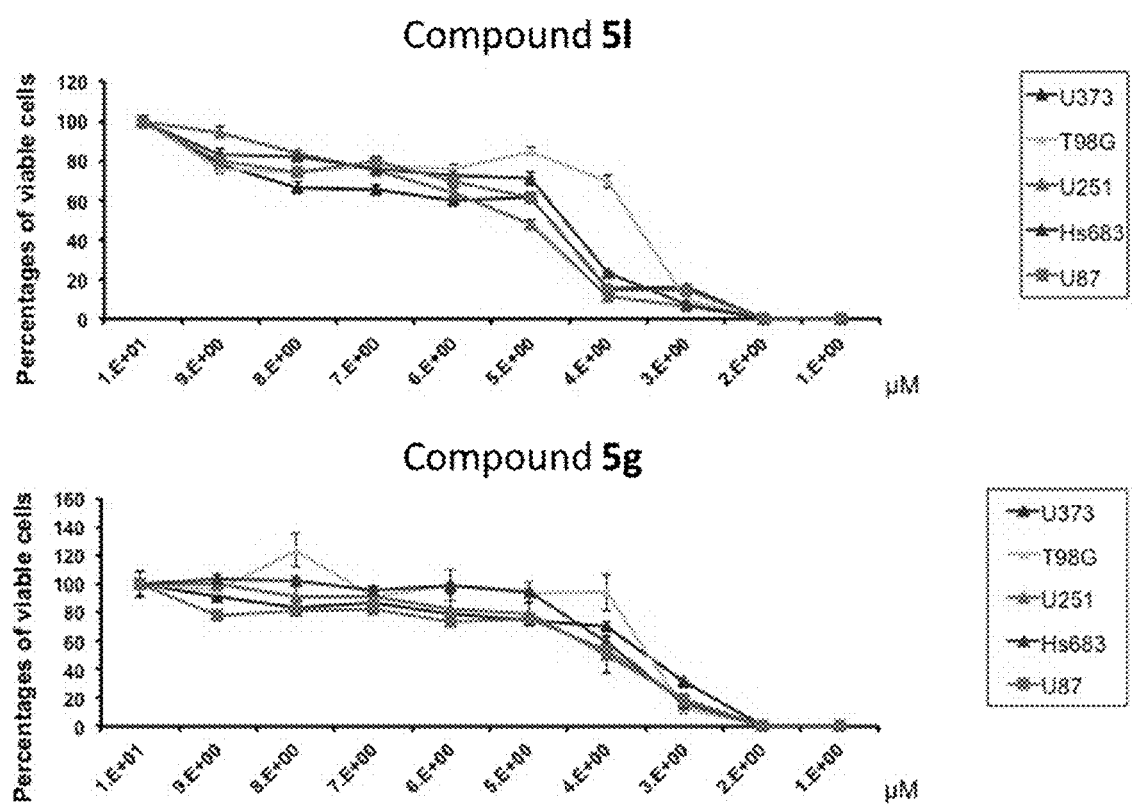
FIG. 8 depicts growth curves of five glioblastoma multiforme (GBM) cell cultures treated with compounds 5l and 5g.
Figure 9:
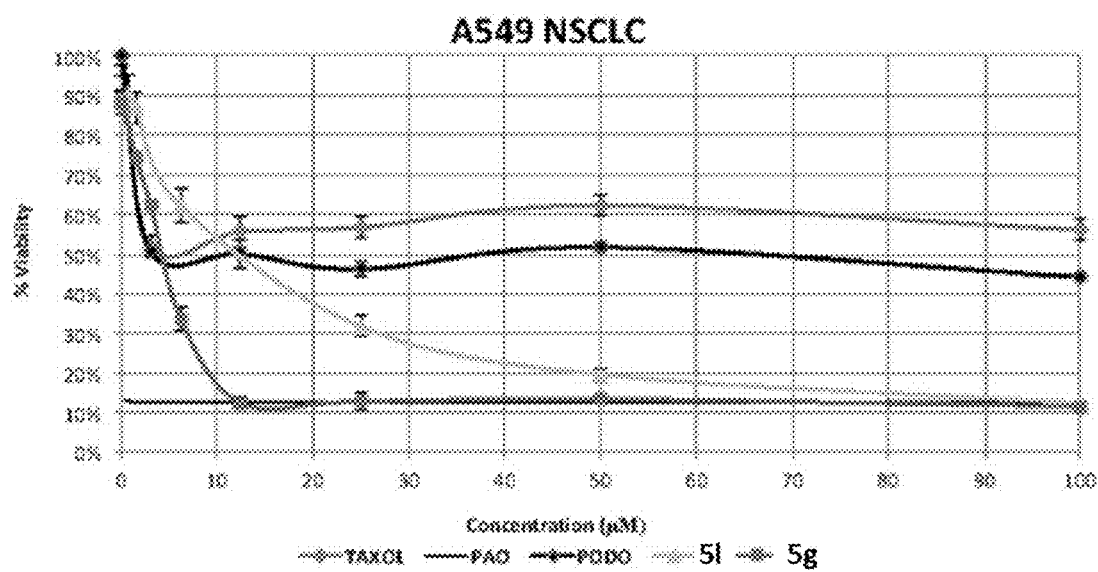
FIG. 9 depicts growth curves of A549 non-small cell lung cancer (NSCLC) cell cultures treated with compound 5l, compound 5g, paclitaxel, phenyl arsine oxide, and podophyllotoxin.

FIG. 8 and FIG. 9 show the dose-dependent effects of compound 5l and 5g against cell populations resistant to proapoptotic agents determined with an MTT assay. FIG. 5 exhibits the growth curves of five glioblastoma multiforme (GBM) cell cultures treated with compounds 5l and 5g. The dose-dependent effects of compounds 5l and 5g were observed in cell lines, including U373, T98G, U251, Hs683, and U87 cell lines. FIG. 9 exhibits the growth curves of A549 NSCLC cell cultures treated with compound 5l, compound 5g, paclitaxel, PAO, and PODO (two independent experiments, each performed in 4 replicates).

EMBODIMENTS

The following non-limiting embodiments provide illustrative examples of the invention, but do not limit the scope of the invention.

Embodiment 1

A method of treating a condition, the method comprising administering to a subject in need thereof a therapeutically-effective amount of a compound of the formula:

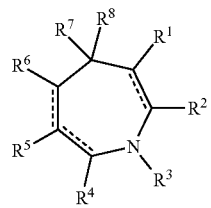

wherein:
- each $R^1$, $R^2$, $R^3$, and $R^4$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted;
- $R^5$ and $R^6$ together with the atoms to which $R^5$ and $R^6$ are bound form a ring that is substituted or unsubstituted;
- $R^7$ and $R^8$ together with the atoms to which $R^7$ and $R^8$ are bound form a ring that is substituted or unsubstituted; and
- each ⇌ is independently a single bond or a double bond, or a pharmaceutically-acceptable salt thereof.

Embodiment 2

The method of embodiment 1, wherein the subject is human.

Embodiment 3

The method of embodiment 1, wherein the condition is cancer.

Embodiment 4

The method of any one of embodiments 1-3, wherein the cancer is melanoma.

Embodiment 5

The method of any one of embodiments 1-3, wherein the cancer is non-small cell lung cancer.

Embodiment 6

The method of any one of embodiments 1-3, wherein the cancer is glioma.

Embodiment 7

The method of any one of embodiments 1-3, wherein the cancer is breast cancer.

Embodiment 8

The method of any one of embodiments 1-3, wherein the cancer is uterine cancer.

Embodiment 9

The method of any one of embodiments 1-3, wherein the cancer is cervical cancer.

Embodiment 10

The method of any one of embodiments 1-9, wherein the condition is drug-resistant cancer.

Embodiment 11

The method of any one of embodiments 1-10, wherein the therapeutically-effective amount is from about 10 mg to about 500 mg.

Embodiment 12

The method of any one of embodiments 1-11, wherein the administration is oral.

Embodiment 13

The method of any one of embodiments 1-11, wherein the administration is intravenous.

Embodiment 14

The method of any one of embodiments 1-11, wherein the administration is subcutaneous.

Embodiment 15

A compound of the formula:

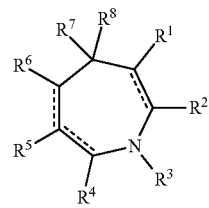

wherein:
- each $R^1$, $R^2$, $R^3$, and $R^4$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted;

$R^5$ and $R^6$ together with the atoms to which $R^5$ and $R^6$ are bound form a ring that is substituted or unsubstituted;

$R^7$ and $R^8$ together with the atoms to which $R^7$ and $R^8$ are bound form a ring that is substituted or unsubstituted; and each ≕ is independently a single bond or a double bond, or a pharmaceutically-acceptable salt thereof.

Embodiment 16

The compound of embodiment 15, wherein $R^7$ and $R^8$ together with the atoms to which $R^7$ and $R^8$ are bound form a 5-, 6-, or 7-membered ring.

Embodiment 17

The compound of any one of embodiments 15 and 16, wherein the compound is of the formula:

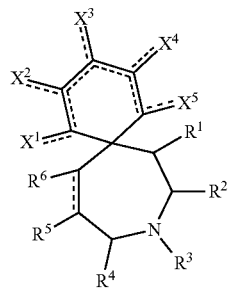

wherein:
each $X^1$, $X^2$, $X^3$, $X^4$, and $X^5$ is independently $CR^{13}R^{14}$, $CHR^{13}R^{14}$, $NR^{13}$, $OR^{13}$, $S^{13}$, O, S, or absent;

wherein each $R^{13}$ and $R^{14}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted.

Embodiment 18

The compound of embodiment 17, wherein any one of $X^1$, $X^2$, $X^3$, $X^4$, and $X^5$ is O and the remaining of $X^1$, $X^2$, $X^3$, $X^4$, and $X^5$ are absent.

Embodiment 19

The compound of any one of embodiments 15 and 16, wherein the compound is of the formula:

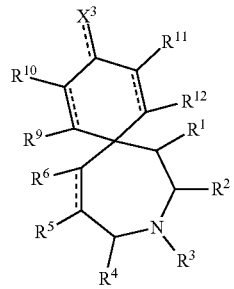

wherein:
each $R^9$, $R^{10}$, $R^{11}$, and $R^{12}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted;

$X^3$ is $CR^{13}R^{14}$, $CHR^{13}R^{14}$, $NR^{13}$, $OR^{13}$, $S^{13}$, O, or S; and
each $R^{13}$ and $R^{14}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted.

Embodiment 20

The compound of embodiment 19, wherein each $R^9$, $R^{10}$, $R^{11}$, and $R^{12}$ is independently H, F, Cl, Br, I, OH, or alkyl.

Embodiment 21

The compound of embodiment 19, wherein each $R^9$, $R^{10}$, $R^{11}$, and $R^{12}$ is hydrogen.

Embodiment 22

The compound of any one of embodiments 15, 16, and 19-21, wherein the compound is of the formula:

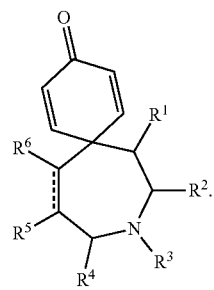

Embodiment 23

The compound of any one of embodiments 15-22, wherein:
- each $R^1$, $R^2$, and $R^4$ is independently hydrogen, halogen, hydroxyl, sulfhydryl, nitro, alkyl, alkenyl, alkynyl, an alkoxy group, an ether group, an ester group, an amine group, or an amide group, any of which is substituted or unsubstituted;
- $R^5$ and $R^6$ together with the atoms to which $R^5$ and $R^6$ are bound form a ring that is substituted or unsubstituted; and
- $R^3$ is alkyl, acyl, or an ester, any of which is substituted or unsubstituted.

Embodiment 24

The compound of any one of embodiments 15-23, wherein each $R^1$, $R^2$, and $R^4$ is independently hydrogen, and $R^3$ is acyl.

Embodiment 25

The compound of any one of embodiments 15-24, wherein $R^5$ and $R^6$ together with the atoms to which $R^5$ and $R^6$ are bound form a 5-membered ring, wherein the 5-membered ring is substituted or unsubstituted.

Embodiment 26

The compound of any one of embodiments 15-25, wherein the compound is of the formula:

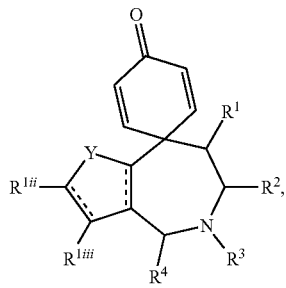

wherein:
- Y is $N(R^{1i})$, S, or O;
- $R^{1i}$ is hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted;
- each $R^{1ii}$ and $R^{1iii}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted; or
- $R^{1ii}$ and $R^{1iii}$ together with the atoms to which $R^{1ii}$ and $R^{1iii}$ are bound form a ring that is substituted or unsubstituted.

Embodiment 27

The compound of any one of embodiments 15-24, wherein $R^5$ and $R^6$ together with the atoms to which $R^5$ and $R^6$ are bound form a 6-membered ring, wherein the 6-membered ring is substituted or unsubstituted.

Embodiment 28

The compound of any one of embodiments 15-24 or 27, wherein the compound is of the formula:

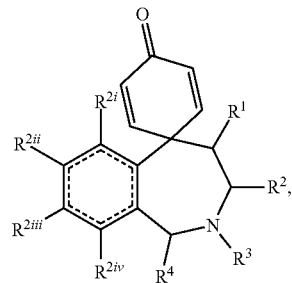

wherein:
- each $R^{2i}$, $R^{2ii}$, $R^{2iii}$, and $R^{2iv}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted; each $R^{2iii}$ and $R^{2iv}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted, and $R^{2i}$ and $R^{2ii}$ together with the atoms to which $R^{2i}$ and $R^{2ii}$ are bound form a ring that is substituted or unsubstituted;
- each $R^{2i}$ and $R^{2iv}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted; and $R^{2ii}$ and $R^{2iii}$ together with the atoms to which $R^{2ii}$ and $R^{2iii}$ are bound form a ring that is substituted or unsubstituted; or each $R^{2i}$ and $R^{2ii}$ is independently hydrogen, halogen, hydroxyl, sulfhydryl, nitro, nitroso, cyano, azido, a sulfoxide group, a sulfone group, a sulfonamide group, a sulfonic acid group, an imine group, an acyl group, an acyloxy group, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, aryloxy, arylalkyl, arylalkoxy, heterocyclyl, heterocyclylalkyl, heteroaryl, or heteroarylalkyl, any of which is substituted or unsubstituted; and $R^{2iii}$ and $R^{2iv}$ together with the atoms to which $R^{2iii}$ and $R^{2iv}$ are bound form a ring that is substituted or unsubstituted.

Embodiment 29

The compound of any one of embodiments 15-26, wherein the compound is of the formula:

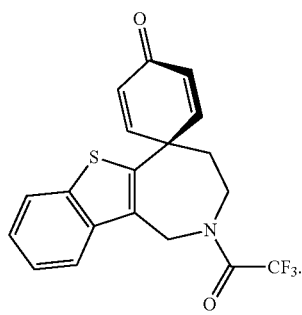

Embodiment 101

A method for treating a condition, the method comprising administering to a subject in need thereof a therapeutically-effective amount of a compound of the formula:

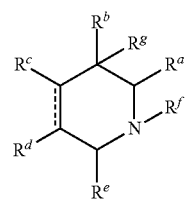

wherein:
$R^a$ and $R^b$ together with the atoms to which $R^a$ and $R^b$ are bound form a ring;
$R^c$ and $R^d$ together with the atoms to which $R^c$ and $R^d$ are bound form a ring;

$R^e$ is alkyl, alkoxy, hydroxyl, or an amine group, any of which is substituted or unsubstituted, or H;
$R^f$ and $R^g$ together with the atoms to which $R^f$ and $R^g$ are bound form a ring; and
each ==== is independently a single bond or a double bond,
or a pharmaceutically-acceptable salt thereof.

Embodiment 102

The method of embodiment 101, wherein the subject is human.

Embodiment 103

The method of any one of embodiments 101-102, wherein the condition is cancer.

Embodiment 104

The method of embodiment 103, wherein the cancer is melanoma.

Embodiment 105

The method of embodiment 103, wherein the cancer is non-small cell lung cancer.

Embodiment 106

The method of embodiment 103, wherein the cancer is glioma.

Embodiment 107

The method of any one of embodiments 101-106, wherein the condition is drug-resistant cancer.

Embodiment 108

The method of any one of embodiments 101-107, wherein the therapeutically-effective amount is from about 10 mg to about 500 mg.

Embodiment 109

The method of any one of embodiments 101-108, wherein the administration is oral.

Embodiment 110

The method of any one of embodiments 101-108, wherein the administration is intravenous.

Embodiment 111

The method of any one of embodiments 101-108, wherein the administration is subcutaneous.

Embodiment 112

A compound of the formula:

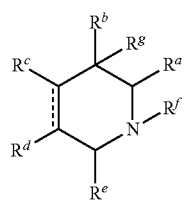

wherein:
 R$^a$ and R$^b$ together with the atoms to which R$^a$ and R$^b$ are bound form a ring;
 R$^c$ and R$^d$ together with the atoms to which R$^c$ and R$^d$ are bound form a ring;
 R$^e$ is alkyl, alkoxy, hydroxyl, or an amine group, any of which is substituted or unsubstituted, or H;
 R$^f$ and R$^g$ together with the atoms to which R$^f$ and R$^g$ are bound form a ring; and
 each ==== is independently a single bond or a double bond,
or a pharmaceutically-acceptable salt thereof, wherein the compound is not:

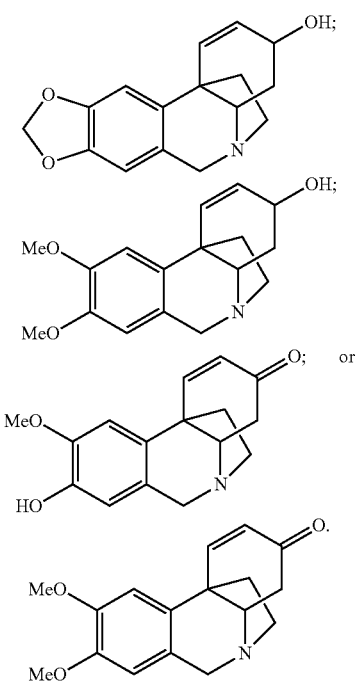

Embodiment 113

The compound of embodiment 112, wherein the compound is of the formula:

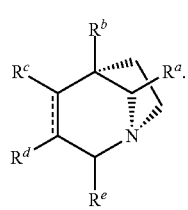

Embodiment 114

The compound of any one of embodiments 112-113, wherein ==== is a double bond.

Embodiment 115

The compound of any one of embodiments 112-114, wherein R$^a$ and R$^b$ together with the atoms to which R$^a$ and R$^b$ are bound form a 6- or 7-membered ring, wherein the 6- or 7-membered ring is substituted or unsubstituted.

Embodiment 116

The compound of any one of embodiments 112-115, wherein R$^a$ and R$^b$ together with the atoms to which R$^a$ and R$^b$ are bound form a 6- or 7-membered carbocycle having 3 sp$^2$ carbon atoms, wherein the 6- or 7-membered carbocycle is substituted or unsubstituted.

Embodiment 117

The compound of any one of embodiments 112-115, wherein R$^a$ and R$^b$ together with the atoms to which R$^a$ and R$^b$ are bound form a 7-membered heterocycle having 3 sp$^2$ carbon atoms, wherein the 7-membered heterocycle is substituted or unsubstituted.

Embodiment 118

The compound of any one of embodiments 112-115, wherein R$^a$ and R$^b$ together with the atoms to which R$^a$ and R$^b$ are bound form a 6- or 7-membered ring having 2 sp$^2$ carbon atoms, wherein the 6- or 7-membered ring is substituted with a hydroxyl group.

Embodiment 119

The compound of any one of embodiments 112-117, wherein the ring formed by R$^a$ and R$^b$ together with the atoms to which R$^a$ and R$^b$ are bound is substituted with a hydroxyl group.

Embodiment 120

The compound of any one of embodiments 112-119, wherein the ring formed by R$^a$ and R$^b$ together with the atoms to which R$^a$ and R$^b$ are bound is substituted with a halogen.

Embodiment 121

The compound of any one of embodiments 112-120, wherein the ring formed by R$^a$ and R$^b$ together with the atoms to which R$^a$ and R$^b$ are bound is substituted with bromine.

Embodiment 122

The compound of any one of embodiments 112-121, wherein R$^c$ and R$^d$ together with the atoms to which R$^c$ and R$^d$ are bound form an aryl ring that is substituted or unsubstituted.

Embodiment 123

The compound of any one of embodiments 112-121, wherein R$^c$ and R$^d$ together with the atoms to which R$^c$ and R$^d$ are bound form a heteroaryl ring that is substituted or unsubstituted.

Embodiment 124

The compound of any one of embodiments 112-121, wherein $R^c$ and $R^d$ together with the atoms to which $R^c$ and $R^d$ are bound form a heterocyclic ring that is substituted or unsubstituted.

Embodiment 125

The compound of any one of embodiments 112-124, wherein $R^c$ and $R^d$ together with the atoms to which $R^c$ and $R^d$ are bound form a bicyclic ring that is substituted or unsubstituted.

Embodiment 126

The compound of any one of embodiments 112-122, and 125, wherein the compound is of the formula:

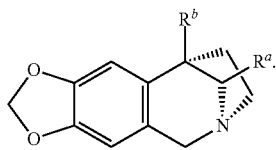

Embodiment 127

The compound of any one of embodiments 112-122, and 125, wherein $R^c$ and $R^d$ together with the atoms to which $R^c$ and $R^d$ are bound form a benzo group that is substituted or unsubstituted.

Embodiment 128

The compound of embodiment 127, wherein the benzo group is substituted with one benzyl group.

Embodiment 129

The compound of any one of embodiments 112-121, wherein $R^c$ and $R^d$ together with the atoms to which $R^c$ and $R^d$ are bound form a benzothiophene group that is substituted or unsubstituted.

Embodiment 130

The compound of any one of embodiments 112-125, wherein $R^e$ is H.

Embodiment 131

The compound of any one of embodiments 112-121, wherein the compound is of the formula:

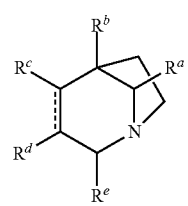

wherein:
$R^c$ and $R^d$ together with the atoms to which $R^c$ and $R^d$ are bound form a carbocycle that is substituted or unsubstituted; and
$R^e$ is H.

Embodiment 132

The compound of any one of embodiments 112-116, wherein the compound is of the formula:

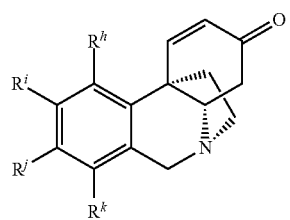

wherein each $R^h$, $R^i$, $R^j$, and $R^k$ is independently H, halo-, O(alkyl) or O(aryl), or any of $R^h$ and $R^i$, $R^i$ and $R^j$, and $R^j$ and $R^k$ together with the atoms to which $R^h$ and $R^i$, $R^i$ and $R^j$, or $R^j$ and $R^k$ are bound form a substituted or unsubstituted ring.

Embodiment 133

The compound of embodiment 132, wherein $R^i$ is OMe and $R^j$ is OBn.

Embodiment 134

The compound of any one of embodiments 112-121, wherein the compound is of the formula:

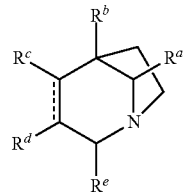

wherein:
$R^c$ and $R^d$ together with the atoms to which $R^c$ and $R^d$ are bound form a heterocycle that is substituted or unsubstituted; and
$R^e$ is H.

Embodiment 135

The compound of any one of embodiments 112-121, 124 and 134, wherein the compound is of the formula:

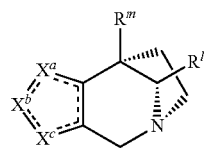

wherein:
R' and R''' together with the atoms to which R' and R''' are bound form a ring that is substituted or unsubstituted;
$X^a$ is S, O, or NH;
$X^b$ is S, O, or C(R'');
$X^c$ is S, O, or C(R°); and
each R'' and R° is H, or R'' and R° together with the atoms to which R'' and R° are bound form a substituted or unsubstituted ring.

Embodiment 136

The compound of embodiment 135, wherein $X^a$ is S, $X^b$ is C(R''), $X^c$ is C(R°), and R'' and R° together with the atoms to which R'' and R° are bound form a ring.

Embodiment 137

The compound of embodiment 136, wherein R'' and R° together with the atoms to which R'' and R° are bound form a benzo group that is substituted or unsubstituted.

What is claimed is:

1. A pharmaceutical composition comprising a pharmaceutically-acceptable excipient and a compound of the formula:

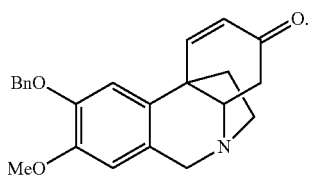 [SMILES: COc1cc2c(cc1OCc1ccccc1)C13C=CC(=O)CC1N(CC3)C2]

2. A pharmaceutical composition comprising a pharmaceutically-acceptable excipient and a compound of the formula:

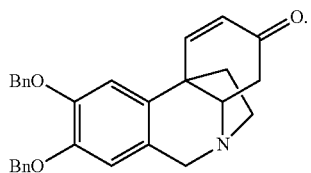

3. A pharmaceutical composition comprising a pharmaceutically-acceptable excipient and a compound of the formula:

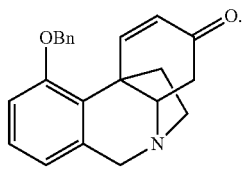 [SMILES: O=C1C=CC23CCN(Cc4cccc(OCc5ccccc5)c42)C3C1]

* * * * *